US009482884B2

(12) United States Patent
Chauveau et al.

(10) Patent No.: US 9,482,884 B2
(45) Date of Patent: Nov. 1, 2016

(54) METHOD OF DETERMINING AN OPHTHALMIC LENS

(75) Inventors: Jean-Pierre Chauveau, Charenton-le-Pont (FR); Frederic Dubois, Charenton-le-Pont (FR); Cyril Guilloux, Charenton-le-Pont (FR); Christian Joncour, Saint Maurice (FR); Melanie Tessieres, Charenton-le-Pont (FR); Helene De Rossi, Charenton-le-Pont (FR)

(73) Assignee: ESSILOR INTERNATIONAL (COMPAGNIE GÉNÉRALE D'OPTIQUE), Charenton-le-Pont (FR)

( * ) Notice: Subject to any disclaimer, the term of this patent is extended or adjusted under 35 U.S.C. 154(b) by 1340 days.

(21) Appl. No.: 14/119,170

(22) PCT Filed: Apr. 19, 2010
(Under 37 CFR 1.47)

(86) PCT No.: PCT/IB2010/051705
§ 371 (c)(1),
(2), (4) Date: Jul. 29, 2014

(87) PCT Pub. No.: WO2010/119435
PCT Pub. Date: Oct. 21, 2010

(65) Prior Publication Data
US 2015/0309338 A1    Oct. 29, 2015

Related U.S. Application Data

(63) Continuation-in-part of application No. PCT/FR2009/000458, filed on Apr. 17, 2009.

(51) Int. Cl.
*A61B 3/10* (2006.01)
*G02C 13/00* (2006.01)
*G02C 7/02* (2006.01)
*A61B 3/00* (2006.01)
*A61B 3/113* (2006.01)

(52) U.S. Cl.
CPC ........... *G02C 13/005* (2013.01); *A61B 3/0025* (2013.01); *A61B 3/1015* (2013.01); *A61B 3/113* (2013.01); *G02C 7/02* (2013.01); *G02C 7/025* (2013.01); *G02C 7/027* (2013.01)

(58) Field of Classification Search
CPC ........... A61B 3/113; A61B 3/04; A61B 3/08
USPC .................. 351/204, 246, 200, 177
See application file for complete search history.

(56) References Cited

U.S. PATENT DOCUMENTS

| 7,434,935 B2 * | 10/2008 | Bonnin | ..................... A61B 3/02 351/159.81 |
| 2010/0128220 A1 * | 5/2010 | Chauveau | ............... A61B 3/111 351/204 |

*Primary Examiner* — Hung Dang
(74) *Attorney, Agent, or Firm* — Polsinelli PC

(57) ABSTRACT

The present disclosure provides systems and methods for determining an ophthalmic lens. In one implementation, three-dimensional coordinates of a center of rotation of the wearer's eye measured on the wearer in binocular vision are received. At least one direction of gaze measured in a natural posture and a determined position of the ophthalmic lens are received. Characteristics of the ophthalmic lens are calculated by using the coordinates measured for the center of rotation of the eye, the determined position of the lens, and the at least one direction of gaze measured in a natural posture. The characteristics of the ophthalmic lens are calculated by positioning a starting ophthalmic lens in the determined position and modifying the starting ophthalmic lens by wavefront analysis and/or optimizing using ray tracing dependent on the coordinates measured for the center of rotation of the eye and the determined position of the lens.

20 Claims, 18 Drawing Sheets

METHOD OF DETERMINING AN OPHTHALMIC LENS

CROSS-REFERENCE TO RELATED APPLICATIONS

This application is a national stage filing pursuant to 35 U.S.C. §371 of International Application No. PCT/IB 2010/051705, filed 19 Apr. 2010 and entitled "Method for Determining an Ophthalmic Lens," which claims priority to International Application No. PCT/FR 2009/000458, filed 17 Apr. 2009 and entitled "Method for Determining an Ophthalmic Lens."

BACKGROUND OF THE INVENTION

The present invention relates to a method for determining an ophthalmic lens for a wearer. The method can be applied interchangeably to a unifocal or multifocal prescription. It also applies to microstructured lenses (pixelated lenses, diffractive lenses, Fresnel lenses and so on), adaptive lenses, graded index lenses and more generally any type of ophthalmic lens.

The invention also extends to the method of calculating the parameters for trimming and manufacturing an ophthalmic lens obtained by the method of determination.

A wearer can be prescribed a power correction, which is positive or negative (hyperopic or myopic wearer); the lens used for this type of prescription is a spherical lens or an aspheric lens. An astigmatic wearer has, in a plane perpendicular to the direction of gaze, a prescription for power that is different along different axes; the prescription is usually expressed as a prescription for a first power value corresponding to power along a main axis and a second power value along an axis perpendicular to the main axis. The lens used for this type of prescription is a toric or atoric lens. Below, we shall call the proposed correction for such wearers a unifocal prescription.

For presbyopic wearers, the value of the power correction is different for far vision and near vision, because of difficulties of accommodation in conditions of near vision. The prescription thus comprises a power value for far vision and a power addition representative of the power increment between far vision and near vision. Ophthalmic lenses that compensate for presbyopia are multifocal lenses, the most appropriate being progressive multifocal lenses, for which power varies continuously. Also known are bifocal or trifocal lenses, with breaks in continuity on the surface of the lens. Below, we shall call the proposed correction for such wearers a multifocal prescription.

Calculating the front and/or rear faces of multifocal and of unifocal lenses using optimization is known. For example, WO-A-98/12,590 discloses a method for determination by optimization of a set of multifocal ophthalmic lenses. This document proposes defining the set of lenses by considering the optical characteristics of the lenses, and notably power and oblique astigmatism under wearing conditions. The lens is optimized using ray tracing, from an ergorama associating a target object point with each direction of gaze under wearing conditions.

A method is also known from EP-A-0,990,939 for determining by optimization an ophthalmic lens for a wearer having an astigmatism prescription. This document proposes selecting a reference lens and using a ray tracing method and minimizing the difference between residual astigmatism and the astigmatism of the reference lens. The residual astigmatism is defined therein as the difference in amplitude and axis of astigmatism between prescribed astigmatism and the astigmatism generated by the lens. This method allows a better adaptation of lenses to astigmatic lens wearers, avoiding optical aberrations induced by the addition of a toric surface. The calculation is performed in a reference frame linked to the eye, which takes into account the twisting effect on the eye when the wearer looks in a direction that is off-center.

In addition, in recent years, it has been made looked for customizing progressive ophthalmic lenses in order to better meet the needs of each wearer. WO-A-2007/068,819 teaches a method of determining a set of progressive ophthalmic lenses for a given wearer for whom a power addition has been prescribed in conditions of near vision, the method comprising a step consisting in measuring individual physiological parameters of the wearer in conditions of near vision. The method also includes a step of determining an ergorama which associates, on each lens, a point aimed at in each direction of gaze under wearing conditions and a step of determining a target power defect and a target for resulting astigmatism for each gaze direction under wearing conditions, the target power defect and resulting target astigmatism being determined from the measured physiological parameters for the wearer. The method further includes calculating the power required on each lens for the said ergorama by successive iterations to reach the target power defect and target astigmatism defect for each direction of gaze.

There is also known from WO-A-2007/068,818 a method for tailoring the progression length of as lens of progress.

There are also documents which teach measurement of physiological parameters and notably the position of the center of rotation of the eye. Thus, WO-A-2008/132,356 discloses a method for determining the position of the center of rotation of the eye.

U.S. Pat. No. 6,637,880 discloses a method for ray tracing and optimization of a lens, taking into account the distance between as reference point on the rear surface of the lens and the center of rotation of the eye of a wearer. This distance is obtained by adding, firstly, the distance between the reference point on the rear surface and the vertex of the cornea, and, secondly, the distance between the vertex of the cornea and the center of rotation of the eye. The distance between the reference point on the rear surface and the vertex of the cornea is calculated from data relating to the selected frame; this document proposes only considering the shape of the wearer's head, the lens data, characteristics of the frame, and wearing conditions, without providing details regarding calculation. The distance between the vertex of the cornea and the center of rotation of the eye is obtained by measuring the depth of the eye and application of a statistical law, establishing a relation between the depth of the eye and the distance between the vertex of the cornea and the center of rotation of the eye. In this document, the position of the center of rotation of the eye taken into account is consequently not the actual position. This results in the lens obtained by optimisation not perfectly satisfying the wearer.

SUMMARY OF THE INVENTION

There is therefore a need for a method of determining an ophthalmic lens that better satisfies wearers.

For this, the invention provides a method for determining an ophthalmic lens for an eye of a wearer, the method comprising the steps of measuring, on a wearer in binocular vision, three-dimensional coordinates of the center of rotation of the wearer's eye;

measuring at least one direction of gaze in a natural posture;

determining the desired position of the ophthalmic lens;

calculating the characteristics of the ophthalmic lens by using the coordinates measured for the center of rotation of the eye, the determined position of the lens and the at least one direction of gaze measured in a natural posture.

The calculating step can include a step of positioning a starting ophthalmic lens in the determined position, and a step of modifying the starting ophthalmic lens by wavefront analysis.

Alternatively, the calculation step can include a step of positioning a starting ophthalmic lens in the determined position and an optimization step, starting from the starting lens, using ray tracing dependent on the coordinates measured and determined position.

According to one embodiment, the method comprises a step of measuring on the wearer in binocular vision, the position of the pupil of the eye with respect to the center of rotation of the eye and in which the calculation step employs the measured position of the pupil.

According to one embodiment, the calculation step is performed in a reference frame based on the wearer's head, and/or a reference frame based on a spectacle frame, and/or a reference frame based on the wearer's eye.

According to another embodiment, the method further comprises a step of measuring the wearer in binocular vision, three-dimensional coordinates of the center of rotation of each eye of the wearer and in which the calculation step is done in a reference frame that is based on three-dimensional coordinates of the center of rotation of each eye of the wearer.

According to another embodiment, the step of measuring three-dimensional coordinates of the center of rotation of the eye is performed under conditions of natural posture of the wearer.

According to another embodiment, the center of rotation of the eye is the center of optical rotation.

According to embodiments, the at least one direction of gaze measured in a natural posture is the primary direction of gaze and/or the direction of gaze when the wearer is viewing in near vision. Several directions of gaze can be measured in a natural posture.

According to another embodiment, in the step of measuring the at least one direction of gaze, a distance of the lens to the center of rotation of the eye is measured corresponding to the distance between the intersection of the primary direction of gaze with the rear face of the lens and the center of rotation of the eye, and at the calculation step, the calculation employs said measured distance.

According to another embodiment, the step of measuring the at least one direction of gaze, an orientation of the lens and a lens position are measured at the calculation step, calculation employs said measured orientation of the lens and position of the lens.

The invention also provides a method for calculating the parameters of mounting and/or trimming of an ophthalmic lens for a wearer and a spectacle frame chosen by the wearer, comprising the steps of determining an ophthalmic lens according to the method of the invention;

measuring the position of the spectacle frame in the reference frame used for the measurement and determination steps;

calculating parameters for mounting and/or trimming of the ophthalmic lens according to the position of the lens and the spectacle frame in the reference frame.

The invention also provides a method of simulating an image seen by a wearer through an ophthalmic lens, comprising the steps of measuring, on a wearer in binocular vision, three-dimensional coordinates of the center of rotation of the wearer's eye;

measuring at least one direction of gaze in a natural posture, positioning of the lens;

the steps of measuring and positioning taking place in or being reduced to the same reference frame, calculating an image seen by the wearer using ray tracing, taking into account the measured position of the center of rotation of the eye, the direction of gaze measured in a natural posture and position of the lens.

According to one embodiment, the simulation method comprises a step of measuring, in the reference frame, the position of the pupil of the eye and wherein the calculation step employs the measured position of the pupil.

The invention also provides a method for producing an ophthalmic lens, comprising the steps of:

measuring on a wearer in binocular vision, three-dimensional coordinates of the center of rotation of the wearer's eye and the position of a spectacle frame chosen by the wearer, in the same reference frame, at a first location;

measuring at least one direction of gaze in a natural posture, transmitting the measured coordinates and position to a second location;

determining the lens by calculation using the measured coordinates and position, at the second location, and manufacturing the lens so determined.

According to an embodiment, the method for producing further includes a step of measuring angles representing the natural posture of the wearer in the reference frame at the first location, in which the transmission step includes the transmission of measured angles and posture, and the determination step employs the measured angles of posture.

According to another embodiment, the method for producing further comprises a step of:

measuring the position of the spectacle frame in the reference frame used for the determination;

calculating trimming parameters for the ophthalmic lens as a function of the position of the lens and the spectacle frame in the reference frame, and trimming of the lens.

The invention also provide a data set comprising:

three-dimensional coordinates measured on a wearer in binocular vision, in a reference frame, or the center of rotation of one eye of a wearer;

angles at representative of the natural posture of the wearer in the same reference frame;

the position of a spectacle frame in the same reference frame.

The invention also provides a simulator of an image seen by a wearer through an ophthalmic lens, the simulator comprising calculation means adapted to implement the simulation method according to the invention and means for displaying the image calculated by the calculation means.

The invention also provides a computer program comprising program means for performing the steps of the method for determining an ophthalmic lens according to the invention, when said program is run on a computer, as well as a computer program product comprising program code means stored on a medium readable by a computer, to implement the steps of the method of determining an ophthalmic lens according to the invention, when said program product is run on a computer.

The invention also provides a computer program comprising program means for performing the steps of the method for simulation according to the invention, when said program is run on a computer, together with a computer program product comprising program code means stored on a medium readable by a computer to implement the stimulation method according to the invention, when said program product is run on a computer.

In one alternative embodiment, the method for determining an ophthalmic lens as described above is characterized in that during the calculation step the characteristics of the ophthalmic lens are calculated by local modification of the ophthalmic lens at the point of impact with the average ray passing through the center of rotation of the eye measured for a given direction of gaze.

Other features and advantages of the invention will become apparent on reading the following detailed description of embodiments of the invention, given by way of example only and with reference to the drawings.

DETAILED DESCRIPTION OF PREFERRED EMBODIMENTS

Figure 22:
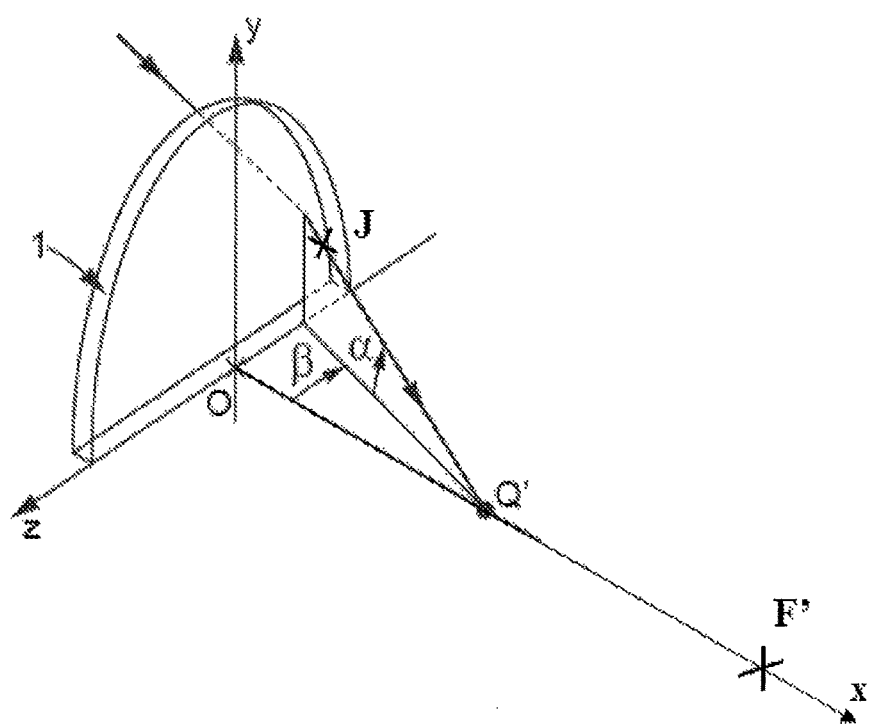
FIGS. 22 to 24 show diagrammatically an eye and lens optical system.
Figure 23:
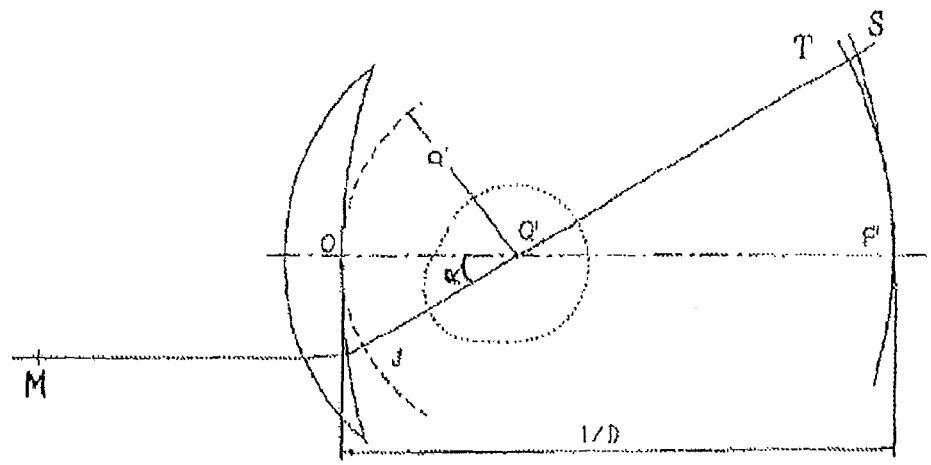
Figure 24:
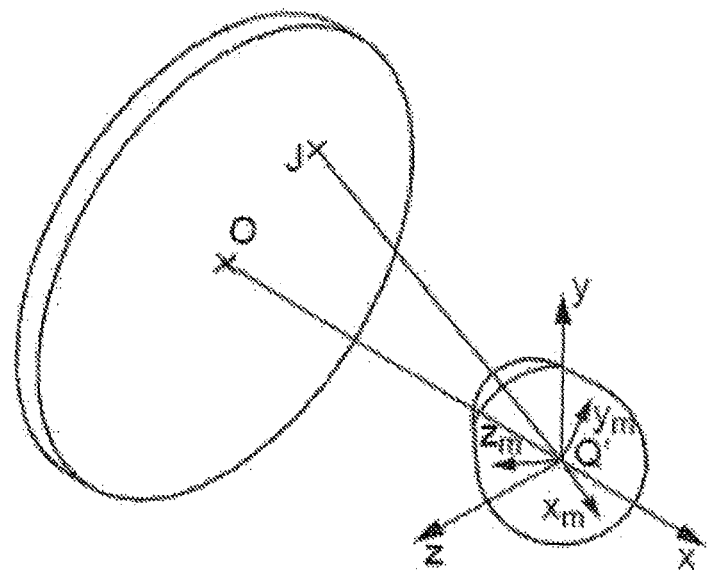

FIGS. 22-24 are diagrams of eye and lens optical systems, to illustrate the definitions used in the description. More specifically, FIG. 22 is a diagram showing a perspective view of a system illustrating the parameters $\alpha$ and $\beta$ used to define a direction of gaze. FIG. 23 is a view in a vertical plane parallel to a front-back axis of the wearer's head and passing through the center of rotation of the eye in a case where the parameter $\beta$ is 0.

We call Q' the center of rotation of the eye; axis Q'F', shown in FIG. 23 in phantom, is the horizontal axis through the center of rotation of the eye and extending ahead of the wearer—in other words the axis Q'F' is the primary direction of gaze. This axis intersects the complex surface of the lens at a point called the fitting cross, which is marked on the lens to allow positioning of the lens by an optician. We define the point O, the intersection of the rear surface of the lens and the axis Q'F'. We define a sphere of the vertices, with center Q' and ray q', which is tangential to the rear surface of the lens at a point on the horizontal axis.

A given direction of gaze—shown in solid lines in FIG. 23—corresponds to a position of the eye in rotation about Q' and at a point J on the sphere of the vertices; angle $\beta$ is the angle between axis Q'F' and the projection of the straight line Q'J on the horizontal plane containing the axis Q'F'; this angle can be seen on the diagram in FIG. 22. The angle $\alpha$ is the angle between the axis and the projection of straight line Q'J on the horizontal plane containing the axis Q'F'; this angle can be seen in the diagrams of FIGS. 22 and 23. A given direction of gaze consequently corresponds to a point J on the sphere of the vertices or a pair of angles ($\alpha$, $\beta$). The more positive the value of the angle of lowering of the gaze $\alpha$, the more the gaze is lowered, and the more the value is negative, the more the gaze rises.

The image of a point in the object space in a direction of gaze, and at a given object distance, is formed between two points S and T corresponding to minimum and maximum focal lengths, which, in the case of surfaces of revolution, would be sagittal and tangential focal lengths. On the optical axis, the image of a point in the object space at infinity is formed at the point F'. The distance D is the focal length of the eye-lens system.

What is called an ergorama is a function that associates with each direction of gaze the usual distance of the object point. Typically, for far vision along the primary direction of gaze, the object point is at infinity. In conditions of near vision, in a direction substantially corresponding to an angle $\alpha$ of about 35° and at an angle $\beta$ of absolute value of the order of 5° towards the nasal side, the object distance is on the order of from 30 to 50 cm. For more details on a possible definition of an ergorama, reference can be made to FR-A-2,753,805 (corresponding to U.S. Pat. No. 6,318,859). This document describes a ergorama, its definition and method of modeling. One particular ergorama consists in only taking points that are at infinity. For the method of the invention, one can consider the points to be at infinity or not. The ergorama can also be a function of the wearer's ametropia.

Using these elements, we can define a power and an astigmatism in each direction of gaze. For a direction of gaze ($\alpha$, $\beta$), we consider an object point M at an object distance given by the ergorama. In the object space, we define, for the point M on the corresponding light ray, an object proximity ProxO as the inverse of the distance MJ between the point M and the point J of the sphere of the vertices:

$$\text{Prox}O = 1/MJ$$

This allows a calculation of the object proximity through a thin lens approximation at any point on the sphere of the vertices used for determining the ergorama. For an actual lens, one can, using a ray tracing program, consider the object proximity to be the inverse of the distance between the object and the front surface of the lens, on the corresponding ray.

Always for the same direction of gaze (α, β), the image of a point M having a given object proximity is formed between two points S and T corresponding respectively to minimum and maximum focal lengths (which, in the case of surfaces of revolution would be sagittal and tangential focal lengths). We call the image proximity for a point M, the quantity ProxI:

$$ProxI = \frac{1}{2}\left(\frac{1}{JT} + \frac{1}{JS}\right)$$

By analogy with the case of a thin lens, we thus define, for a given direction of gaze and for a given object proximity, i.e. a point in the object space on the corresponding light ray, an optical power Pui as the sum of image proximity and object proximity:

Pui=ProxO+ProxI

With the same notations, we define in each direction of gaze and for a given object proximity, an astigmatism Ast as:

$$Ast = \left|\frac{1}{JT} - \frac{1}{JS}\right|$$

This definition corresponds to the astigmatism of the beam of rays created by the lens. Note that the definition provides, in the primary direction of gaze, the conventional value for astigmatism. The angle of astigmatism, commonly called axis is the angle γ. The angle γ is measured in the eye's reference frame $\{Q', x_m, y_m, z_m\}$. It corresponds to the angle at which the image S or T is formed depending on the convention used in relation to the direction $z_m$ in the plane $(Q', z_m, y_m)$.

In this way, we obtain possible definitions of optical power and astigmatism of the lens under wearing conditions, which can be calculated as explained in the paper by B. Bourdoncle and al., "Ray tracing through progressive ophthalmic lenses," 1990 International Lens Design Conference, DT Moore publ., Proc. Soc. Photo. Opt. Instrum. Eng. By the expression standard wearing conditions, we mean the position of the lens with respect to the eye of an average wearer, defined notably by a pantoscopic angle of −8°, a lens-eye distance of 12 mm and an angle of curvature of 0 degrees. We could also use other conditions. We can calculate the wearing parameters for a given lens using a ray tracing program. Optical power and astigmatism can also be calculated so that the prescription is achieved at the reference point for far vision either for a wearer wearing his glasses under wearing conditions, or as measured using apparatus known as a frontofocometer.

FIG. 24 shows a perspective view for a configuration where the parameters α and β are non-zero. This highlights the effect of rotation of the eye by showing a fixed reference frame {x, y, z} and a reference frame $\{x_m, y_m, z_m\}$ linked to the eye. The reference frame {x, y, z} has its origin in the point Q'. The x-axis is the axis Q'O and is directed from the lens towards the eye. The y-axis is vertical and directed upwards. The z axis is such that the reference frame {x, y, z} is direct orthonormal. The reference frame $\{x_m, y_m, z_m\}$ is linked to the eye and has its center at the point Q'. Axis $x_m$ corresponds to the direction JQ' of gaze. Thus, for the primary direction of gaze, the two reference frames {x, y, z} and $\{x_m, y_m, z_m\}$ coincide.

The invention employs, in order to determine the characteristics of an ophthalmic lens, the position of the center of rotation of the eye and the desired position of the ophthalmic lens with respect to the center of rotation of the eye. At least one direction of gaze in a natural posture is measured. The position of the center of rotation of the eye is measured on the wearer in binocular vision. The characteristics of the lens are calculated using the coordinates of the center of rotation of the eye measured, the position of the desired lens determined with respect to the center of rotation of the eye as well as the direction measured in a natural posture.

The lens obtained by such a method of determining has the advantage of taking into account a very precise position of the center of rotation of the eye. This makes it possible to provide lenses which are better adapted to the lens wearer: the characteristics of the lens are calculated by regions on the lens each adapted to a given direction of gaze which in the case of the invention is the actual direction of gaze of the wearer. This allows an exact power correction for the particular wearer, since, for each direction of gaze the wearer will use a particular area of the lens that has precisely been calculated to be used in this way.

The proposed solution applies not only to progressive multifocal lenses, but also to lenses designed for a unifocal prescription. It is also possible to use the method with multifocal lenses such as bifocal or trifocal lenses. The method of determination applies also to a lens optimized for specific wearing conditions.

We shall describe below the application of the method for the determination of a lens to one of a wearer's eyes; the method can be applied to the determination of a lens for each eye of the wearer. To do this, it suffices to successively calculate each of the lenses, provided that the measurement of the position of the center of rotation of each eye is measured in binocular vision.

Figure 1:
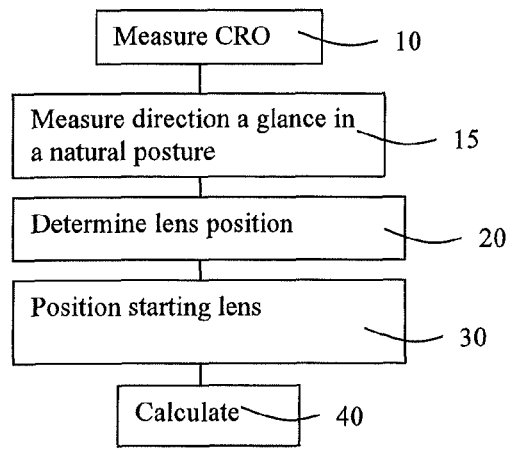
FIG. 1 shows a flowchart of an example of the implementation of a method for determining an ophthalmic lens by analyzing wave front propagation.

FIG. 1 illustrates a flowchart of an example of the implementation of a method for determining an ophthalmic lens for a wearer by analysis of wavefront propagation. The method of determining includes a step 10 consisting in measuring, on the wearer in binocular vision, the three-dimensional coordinates of the center of rotation of one of the wearer's eyes.

The position of the center of rotation of one eye as measured depends on measurement conditions. In particular, measuring three-dimensional coordinates of the center of rotation of the eye on a wearer in binocular vision gives a more accurate measurement of the actual position of the centers of rotation in the same reference frame.

For measuring the three-dimensional coordinates of the center of rotation of the eye, one can use the apparatus described in WO-A-2008/132,356. The invention is not limited to the use of this apparatus, and another apparatus can be used suitable for measuring three-dimensional coordinates of the center of rotation of the eye. In every case, it is essential to the invention that the far measurement of center of rotation of the eye occurs in binocular vision. Advantageously, determining the position of the center of rotation of the eye can be done using several successive measurements, as a way of improving the accuracy of the measuring instrument if necessary.

One can proceed with successive measurements of the position in space (i.e. three-dimensional coordinates) for one eye then the other eye—always in binocular vision. It can also be advantageous to simultaneously measure the position of the center of rotation of the right eye and left eye.

We know, after step 10, the position of the center of rotation of the eye in space. This position is given by three-dimensional coordinates in a reference frame. As explained below, we can make a change of reference frame to facilitate the calculations of the lens.

The determination method according to FIG. 1 further includes a step 15 for measuring at least one direction of gaze in a natural posture. Such a step 15 is more particularly described below.

At step 20, we proceed to a determination of the desired position of the ophthalmic lens. For this determination, we can again use the apparatus described in WO-A-2008/132, 356 by providing the wearer with a frame of his choice, with the test lenses. One can also use any other method, such as for instance a traditional measurement of the position of the lens in the frame chosen by the wearer.

It is advantageous to make this determination on the frame chosen by the wearer, allowing the adaptation of the frame to the wearer, and thus a more accurate measurement of the desired position of the lens in the frame; one could also measure the physical characteristics of the wearer, and use the dimensions measured in advance of the selected frame; this solution consisting in simulating the position of the lens has the advantage of not needing to have the frame available. Determining the position of the lens can consequently result from measurement or from simulation.

We can, at this positioning step, take into account the parameters of mounting and/or of trimming of the lens in a frame. Indeed, these parameters can change the spatial position of the lens in the frame. These parameters include, for example, the location of the lens edge bevel: the lens-eye distance (or lens-rotation center of the eye distance) is not the same if the bevel is positioned at the front or rear face of the lens. The curvature of the glass can, in addition, affect the position (especially if the optician does not to further adjustment of the frame).

This step also calculates the dimensions necessary for centering the lenses
- distance between the centers of rotation of the eye (CROg, CROd) (which advantageously replaces the measurement of interpupillary distance (ISO 13666 standard) with a conventional pupillometer)
- inter-CRO half-distances in the plane of the frame (inter-CRO half-distances should be taken to mean the distance between the projection of the center of rotation of the eye (CRO) in the direction of gaze when the eye is looking straight in front at an object located at eye level with the median line of the frame of the glasses)
- right eye and left eye mounting heights in the plane of the frame It is also advantageous to use the same apparatus for measuring the coordinates of the center of rotation of the eye and for determining the desired position of the ophthalmic lens, as this avoids a change of reference frame, thereby having the same reference frame for the position in space of the center of rotation of the eye and the desired lens. Measurements with different pieces of apparatus are still possible with a simple change of reference frame.

We know, after steps 10, 15 and 20, the desired position of the ophthalmic lens and the position of the center of rotation of the eye. So we know the relative position in space of the lens and the desired center of rotation of the wearer's eye. In the example, we have first determined the position of the center of rotation of the eye at step 10, then a gaze direction in a natural posture for the wearer to step 15, then the desired position of the lens at step 20. It is of course possible to proceed in reverse order: one would obtain in the same way, a relative position in space of the desired lens and the center of rotation of the wearer's eye.

The method of determining further comprises a calculation step the characteristics of the lens, using the coordinates of the center of rotation of the eye and the determined position of the desired lens. In the example in FIG. 1, we can for instance adapt this calculation step a unifocal lens, that is to say a lens for a wearer suffering from nearsightedness or farsightedness, for whom one would traditionally provide a spherical or tonic lens.

The calculation step involves choosing a starting lens, which is for example in case of a unifocal prescription, would be the spherical or tonic lens corresponding to the wearer's prescription. The starting lens is the one that most simplifies the calculation step, but one could use another starting lens.

At step 30, the starting lens is then positioned at the position determined at step 20. This step of positioning does not evolve physically arranging the lens in the frame; it simply involves placing, for the purposes of calculation, the starting lens in the desired position relative to the center of rotation of the eye. In practice, we can use for this positioning a representation of the starting lens in the form of a computer representation. We can proceed with the step of positioning by using one or the other of the reference frames proposed below, and defining the position of the computer representation of the lens in this reference frame. For an astigmatism prescription, of course, we take into account the position of the principal axes of the lens. One can, as explained with reference to step 20, take the trimming/mounting parameters into account when positioning the starting lens.

At step 40, we proceed with calculation of the lens, starting from the thus positioned starting lens, and knowing the position of the center of rotation of the eye and the direction measured in a natural posture at step 15. To this end, we can proceed to an analysis of wave fronts through the lens. The propagation of wave fronts through the lens makes it possible to model the optical function of the lens along with its associated defects and aberrations. The effects of the modifications introduced into the lens (e.g. modification of the front or rear surface in the case of a conventional lens characterized by the phenomena of light refraction or modification for example of phase function in the case of a diffractive lens) can thus be studied and quantified to obtain the optical characteristics desired for the lens to the wearer concerned.

If we take into account the parameters of trimming/mounting of the lens, changing the geometry of the lens can lead to a change in spatial position, if we again apply the trimming/mounting parameters to the modified lens. One can recalculate the parameters and change the lens again. The calculation loop can be stopped when the difference between the old and new parameters is of an order of magnitude that no longer significantly influences the geometry of the new lens. One can also stop the calculation loop in case of discrepancy, and in this case impose other parameters for trimming/mounting.

After leaving step 40, we now have the characteristics of the lens. Since the method takes into account the position of the center of rotation of the eye measured in binocular vision, it can be ensured that the center of rotation of the eye used for the calculation of the lens is very close to the center of rotation of the actual eye, so that the lens is really adapted to the wearer.

Taking into consideration the three-dimensional coordinates of the center of rotation of the wearer's eye in the measurement on the wearer in binocular vision, in the method for determining an ophthalmic lens for an eye of a wearer (monocular determination of an ophthalmic lens) can also significantly improve the comfort of the wearer. This improvement in comfort is related in particular to the fact that it is possible to take into account the segment defined by the center of rotation of the left eye and the center of rotation of the right eye (CROg-CROd). This segment is indeed a factor that can be thus advantageously taken into account in monocular determination of the ophthalmic lens. This segment is used to spatially connect the two eyes of the wearer accurately so that despite monocular calculation of the lens, account can be taken of the relative position of both eyes of the wearer in order to make the calculation even more precise by taking account of the concepts of binocular vision. The two lenses for the same wearer are calculated separately, but this measure allows the calculations to be made one dependent on the other, to improve visual comfort in binocular vision.

Since the method also employs determination of the desired position of the lens, the lens obtained by the method is not affected by a change in position due to the frame. For example, if a wearer has a frame with a large inclination, this inclination is taken into account in determining the characteristics of the lens, so the wearer is provided with a lens adapted to his or her prescription.

Figure 2:
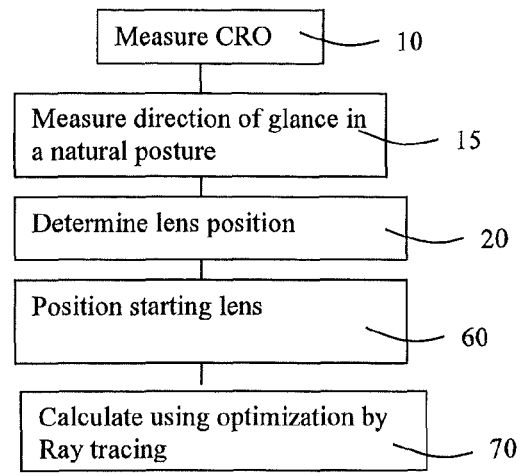
FIG. 2 shows a flowchart of another example of the implementation of a method for determining an ophthalmic lens by optimization using ray tracing.

FIG. 2 illustrates a flowchart of an example of implementation of a method for determining an ophthalmic lens by optimization using ray tracing.

Like in the example in FIG. 1, the method of determining includes a step 10 for measuring, on the wearer in binocular vision, the three-dimensional coordinates of the center of rotation of a wearer's eye, a step 15 for measuring at least one direction of gaze in a natural posture and a step 20 of determining the desired position of the ophthalmic lens. After these three steps, we have the relative position in space, of the center of rotation of the eye and of the lens, as it will actually be worn by the wearer.

The calculation step involves choosing a starting lens. The starting lens is not a physical lens but rather a computer model. The starting lens can be chosen in different ways. This may be the one that most simplifies the optimization step discussed below. But one could also use another starting lens, for example, corresponding to given constraints, of a geometrical nature for example.

At step 60, the starting lens is then positioned in the position determined at step 20. The remarks made above with respect to step 30 apply, mutatis mutandis.

At step 70, a calculation of the lens, from the starting lens and thus positioned is performed, and knowing the position of the center of rotation of the eye. To this end, we can proceed by optimization from the starting lens using ray tracing. Rays used are determined by the center of rotation of the eye as measured and the position of the lens.

Calculation step 70 can be done in various ways and notably by optical optimization using an optimization program as disclosed in EP-A-0990939 or WO-A-2007/017766. As explained with reference to FIG. 1, it is also possible for better accuracy, to take account of the parameters concerning trimming/mounting of the lens in a selected frame.

The calculation step for the characteristics of the lens (steps 30 and 40 in FIG. 1, steps 60 and 70 in FIG. 2) makes it possible to take account in the determination of the lens, of more precise binocular measurement of the actual position of the center of rotation of the eye in a reference frame obtained at step 10 of the measurement. The result is a lens with improved optical characteristics compared to a lens determined without accurately taking into account the three-dimensional coordinates of the center of rotation of the wearer's eye in binocular vision. Here, the expression optical characteristics means image quality perceived by the wearer. The optical characteristics thus include power defect or astigmatism defect.

The calculation step also takes into account the position of the lens, as it will actually be worn by the wearer, which is determined at step 20.

The calculation step also takes into account the direction measured in a natural posture, as done at step 15.

The lens is better suited to the intended wearer. Visual comfort of the wearer is thus maximized.

In the example in FIG. 1 we considered the case of a unifocal prescription to illustrate the choice of starting lens. We can nevertheless apply the solution to wave front analysis for other types of prescriptions (e.g. multifocal prescriptions) and for all types of lenses (conventional lenses just as well as microstructured lenses, adaptive lenses or graded index lenses).

The example in FIG. 2 for its part is particularly suitable for a multifocal prescription: the distribution of rays during ray tracing depending on the region of vision in question. One can also apply the optimization method using ray tracing to unifocal prescriptions, or yet again to an atoric lens, to microstructured lenses (pixelated lenses, diffractive lenses, Fresnel lenses) adaptive lenses or graded index lenses.

The improvement in optical characteristics mentioned above is illustrated by the examples of FIGS. 6 to 13. In this example, we seek to determine a progressive lens for the following prescription:

prescribed sphere: 4 diopters
prescribed cylinder: 0 diopters
axis of 0°.
addition: 2 diopters.

The refractive index of the glass is 1.665 and the diameter of the lens is 65 mm.

The optical characteristics then shown in FIGS. 6-13 were obtained by calculation.

Figure 6:
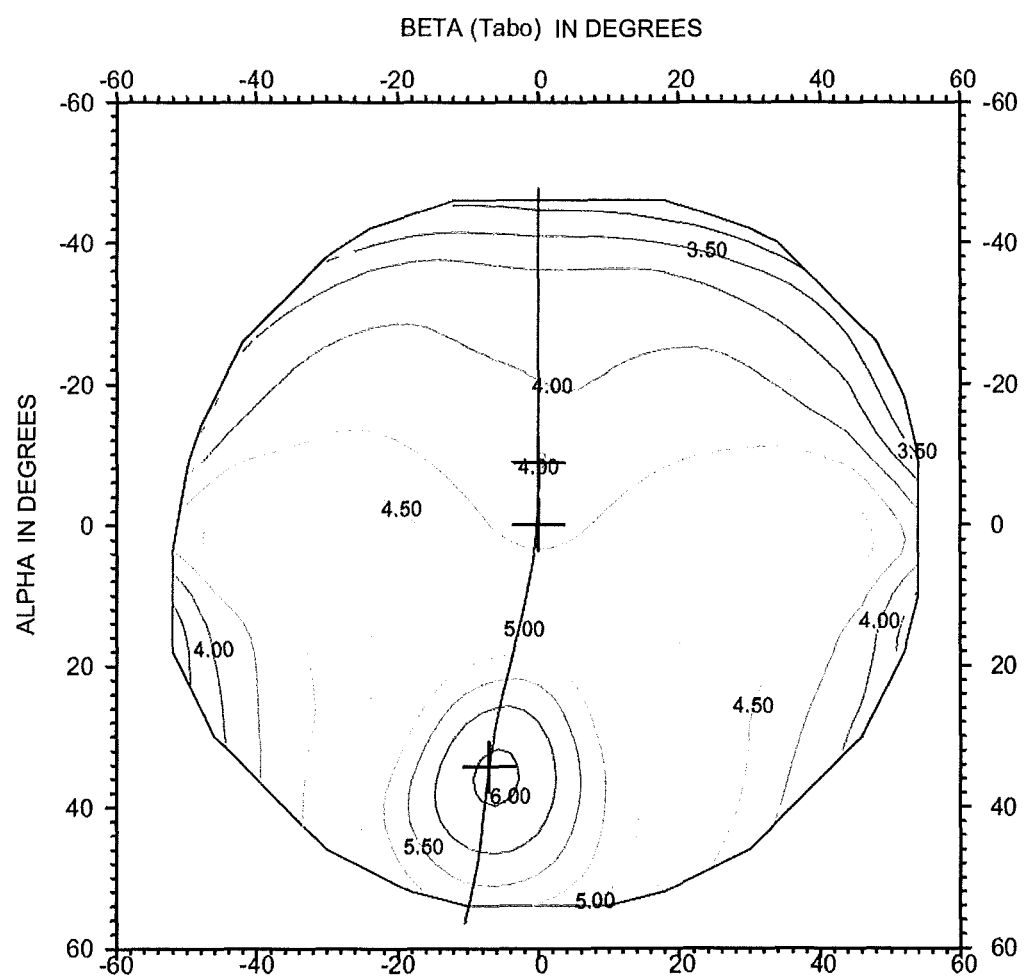
FIGS. 6 and 7 show graphically the optical characteristics of a lens of the prior art for an average wearer.
Figure 7:
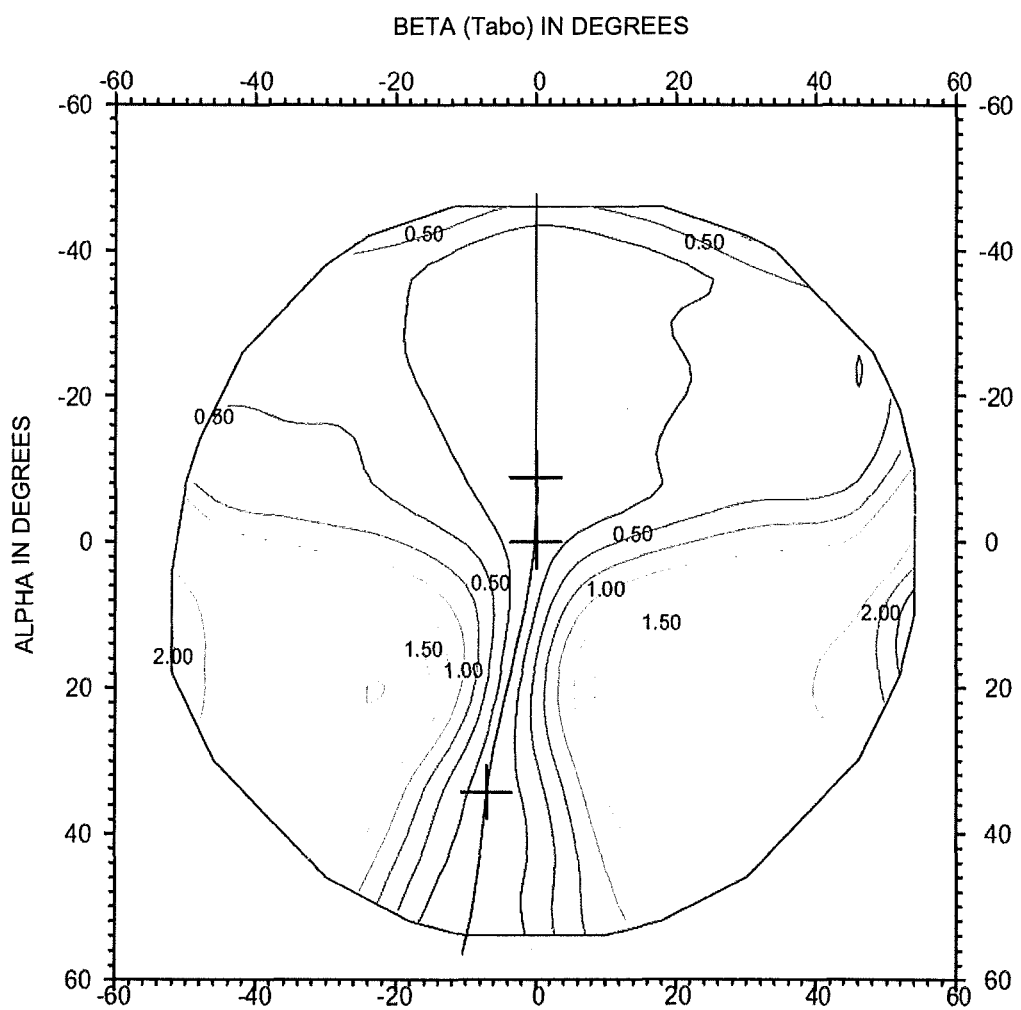

FIGS. 6 and 7 relate to a lens of the prior art for an average wearer for which the lens has been optimized taking into account a theoretical position of the center of rotation of the eye. Here, the term "average wearer" means a wearer for whom the distance between the center of rotation of the eye and the lens is 26 mm, this distance being the sum of the distance between the center of rotation of the eye and the vertex of the cornea and the distance between the vertex of the cornea and the lens, the latter being also called the lens-eye distance. FIG. 6 is a graphical representation of lines of equal power, i.e. the lines formed by points with the same power value. FIG. 6 thus makes it possible to view a map of power. FIG. 7 shows lines of equal astigmatism. FIG. 7 is consequently a graphical representation of astigmatism defect. Power at the far vision point is 4.00 diopters and is 6.04 diopters at the near vision point. The astigmatism defect is 0.00 diopters at the far vision point and 0.13 diopters at the near vision point.

Figure 8:
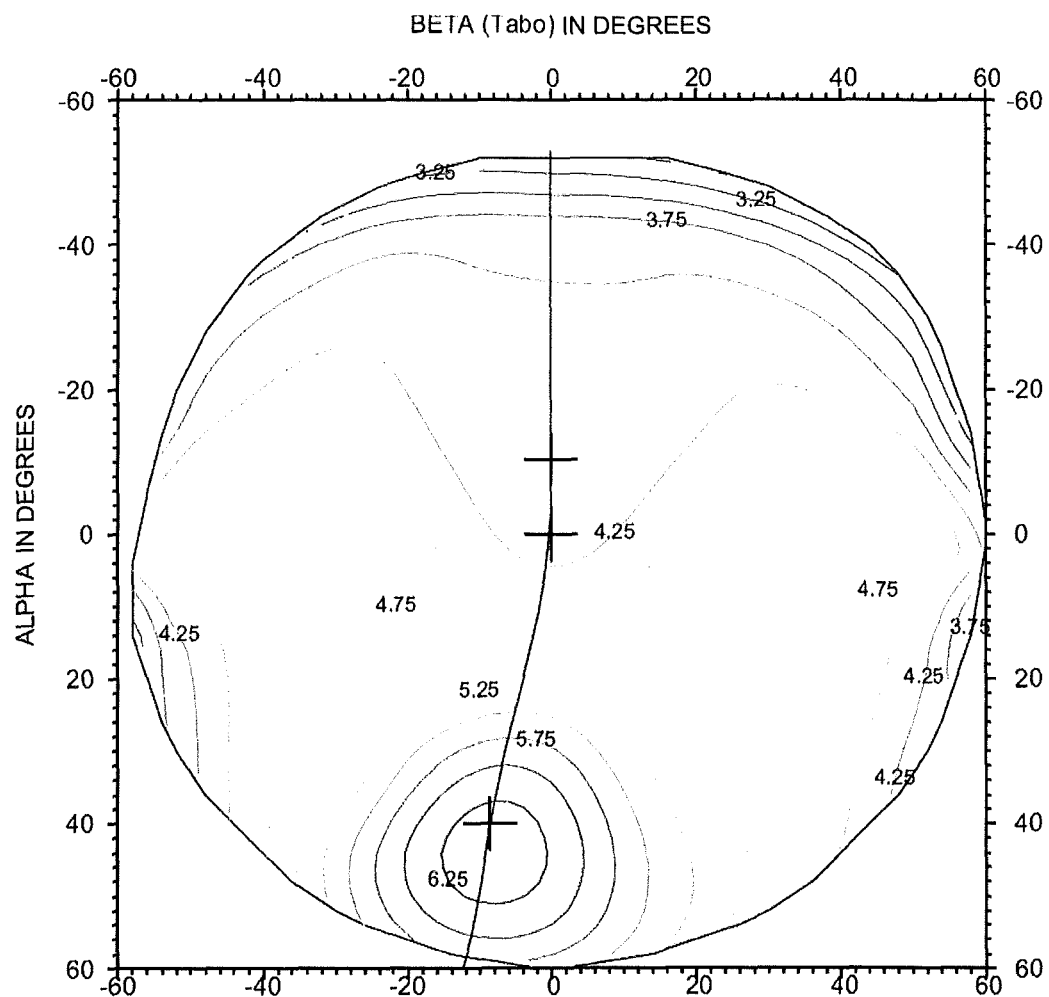
FIGS. 8 to 10 show graphically the optical characteristics of a lens of the prior art for an actual wearer.
Figure 9:
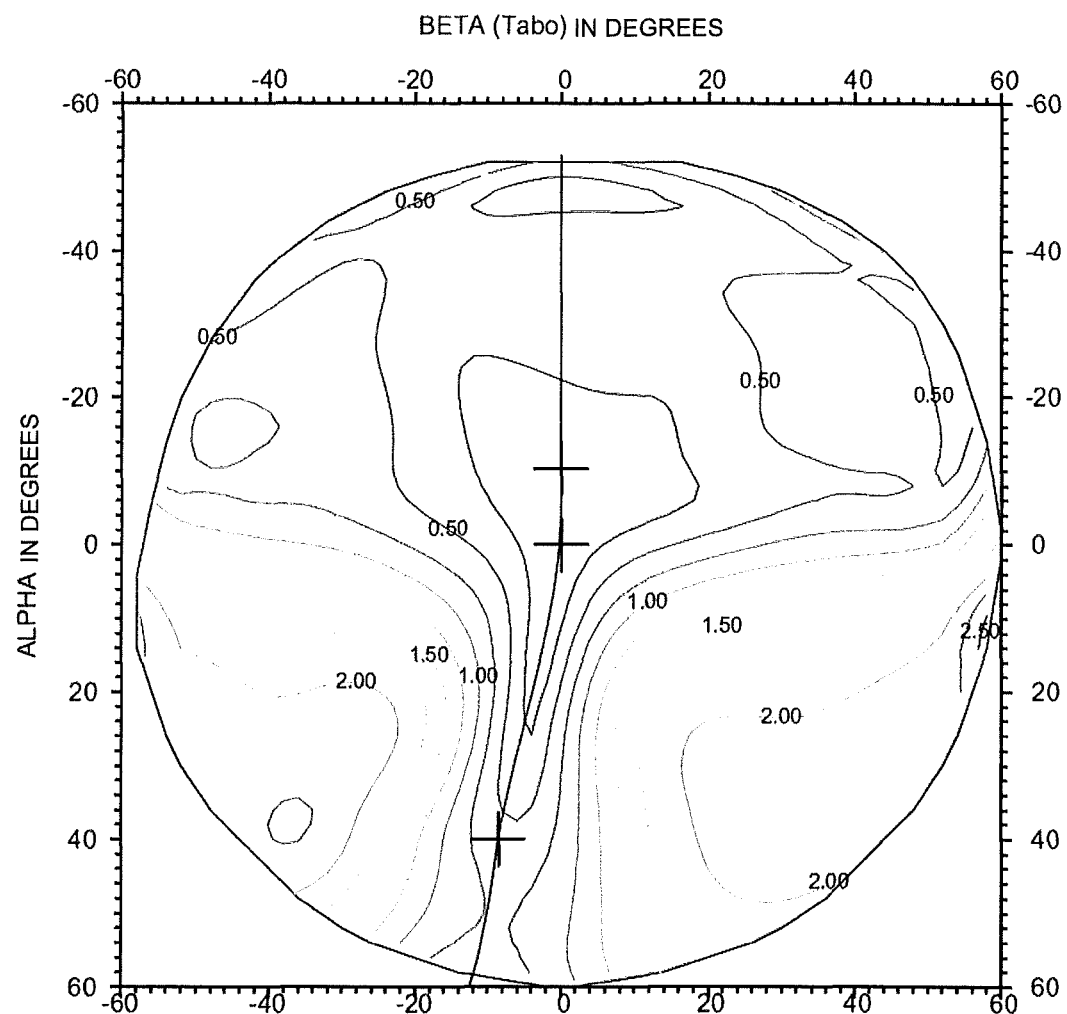
Figure 10:
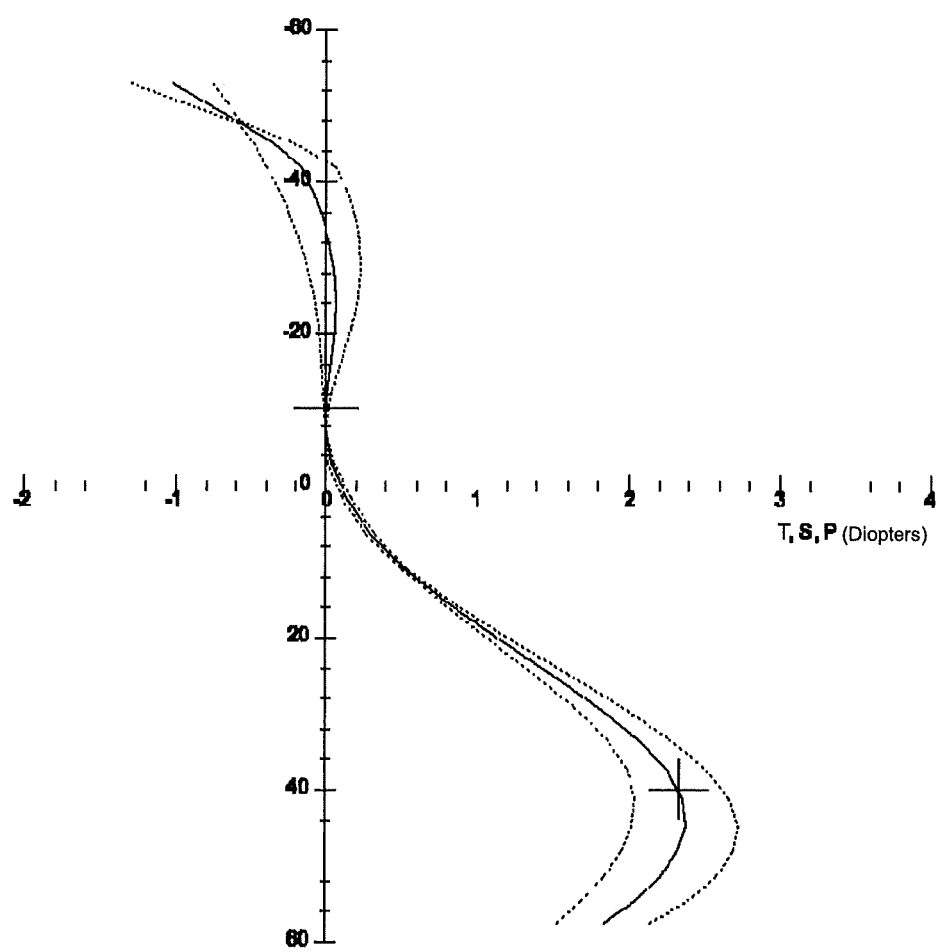

FIGS. 8 and 9 respectively show a power map and a map of astigmatism defect for the same prior art lens (thus still optimized for the average wearer) in the case of an actual wearer. For the actual wearer chosen, the distance between the center of rotation of the eye and the vertex of the cornea is 11 mm and the lens-eye distance is 10 mm. In addition, FIG. 10 shows the power along the meridian, with a definition of power similar to that given in EP-A-0,990,939. The abscissa is graduated in diopters, and the ordinates give the direction of gaze, the solid line shows power and the dashed lines the quantities 1/JT and 1/JS defined in FIG. 1 of EP-A-0,990,939 for distances of objects corresponding to an ergorama representing object point distances in each direction of gaze and simulating an average object space. FIG. 10 consequently gives access to the defect in power and astigmatism along the meridian.

The power in the direction of far vision is 4.02 diopters and is 6.35 diopters in the direction of near vision. The astigmatism defect is 0.03 diopters in the direction of far vision and 0.59 diopters in the direction of near vision. A comparison between FIGS. 6 and 8 shows in particular the appearance of an error in power in conditions of near vision. A comparison of FIGS. 7 and 9 shows that when an actual wearer is considered, astigmatism may vary. In particular, hi this example the fields of astigmatism are not as clear-cut in far vision and in conditions of near vision than when an average wearer was considered.

Figure 11:
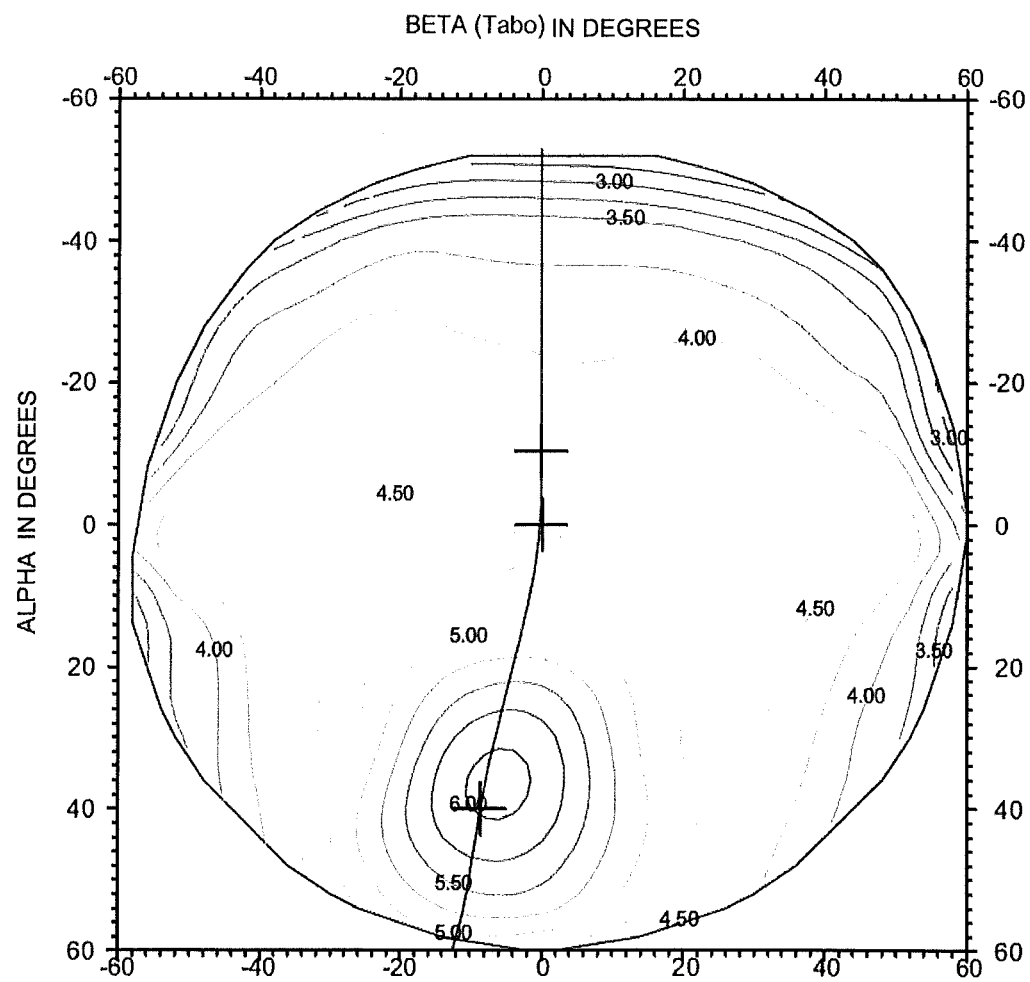
FIGS. 11 to 13 show graphically the optical characteristics of a lens determined by the method of determining for an actual wearer.
Figure 12:
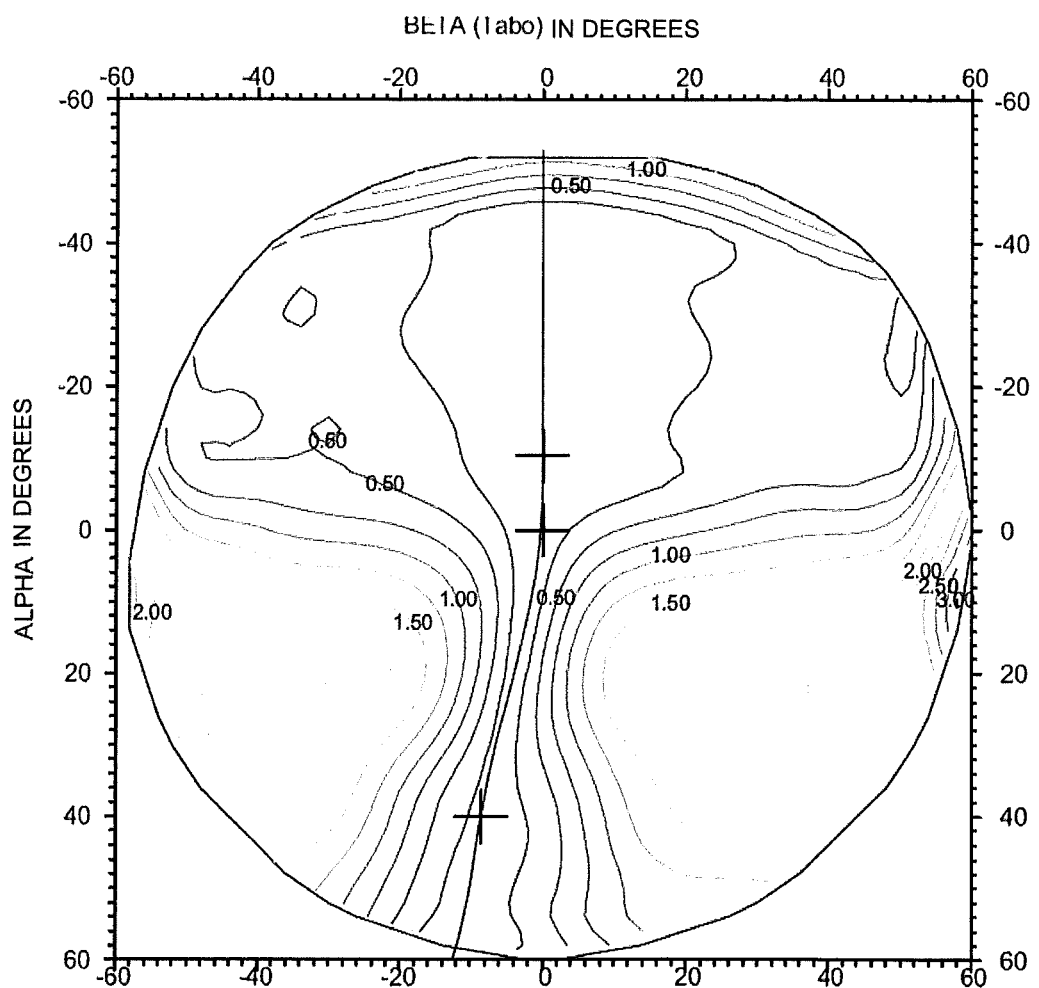
Figure 13:
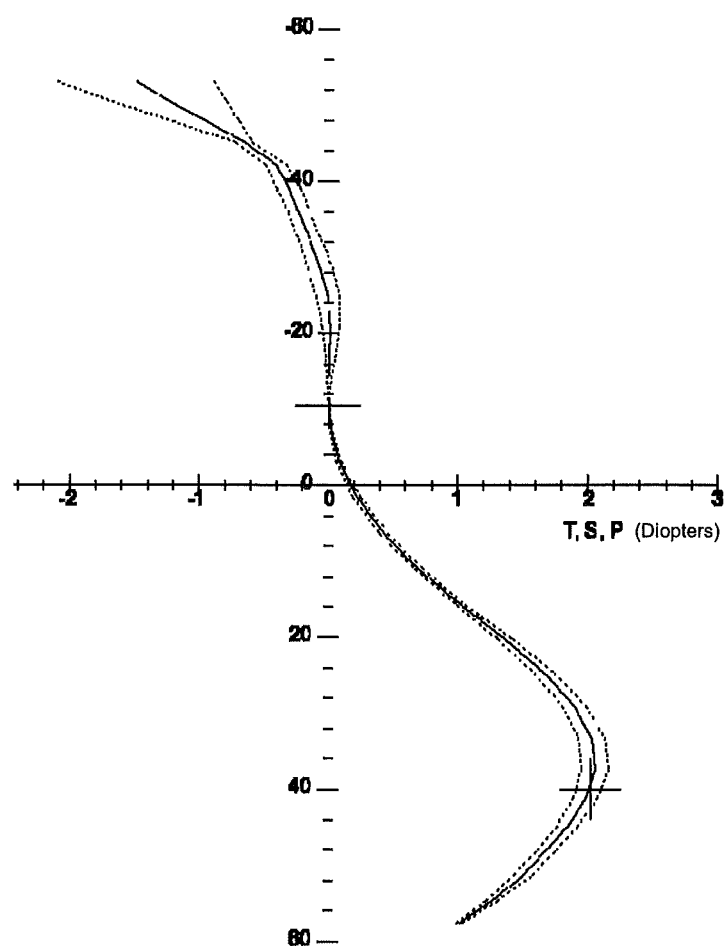

FIGS. 11 and 12 show respectively a map of power and a map of astigmatism defect for a lens obtained by the method of determination according to the invention for the same actual wearer. FIG. 13 illustrates the defect in power and astigmatism along the meridian for the lens wearer for the same actual wearer. The lens was determined as proposed in reference to FIG. 2 using ray tracing by positioning the lens in the desired position in space relative to the center of rotation of the eye, measured for the actual wearer in binocular vision. In FIG. 11, the power in the direction of far vision is 4.00 diopters and is 6.03 diopters in the direction of near vision. In FIG. 13, the astigmatism defect is 0.00 diopters in the direction of far vision and 0.20 diopters in the direction of near vision. The optical performance obtained for the lens using the method of determining according to the invention is comparable to the performance obtained in the case of FIGS. 6 and 7. Comparing FIG. 10 with FIG. 13 also shows that the lens optimized according to the present method of determining has optical characteristics that are better than the lens of the prior art. The result is a lens obtained by the method of determining that is better suited to the wearer than the lens of the prior art.

To further improve the optical characteristics of the lens, it is advantageous for the center of rotation of the eye measured at step 10 of the measurement to be the center of optical rotation rather than the mechanical center of rotation. *Heinz Diepes, Refraktionsbestimmung*, ISBN 3-922269-50-8, Doz Verlag, *Optische Fachveröffentlichung GmbH Heidelberg* contains the definition known to the skilled person for optical center of rotation and mechanical center of rotation. Indeed, in practice, the mean ray arriving at the wearer's eye passes through the center of optical rotation. The three-dimensional coordinates of the center of optical rotation can be determined, in binocular vision by simultaneous binocular fixing of a target.

In the example in FIG. 2, the method may also include a measuring step in the reference frame of the position of the pupil of the eye. The calculation step can then use the measured pupil position. This allows to better take account of aberrations that arise from the pupil. This results in improvement in the image perceived by the wearer which consequently includes fewer aberrations.

Several different reference frames can be considered for the implementation of the calculation step. In particular, the reference frame may be a reference frame associated with the wearer's head. Such a reference frame has the advantage of being easily accessible during the step of measuring the position of the center of rotation of the eye; it remains just as readily accessible when performing the determination step.

When measuring step 10 is carried out on a wearer who is wearing a spectacle frame, the reference frame may be based on the spectacle frame. This provides a reference frame that is independent of the wearer. Measuring the position of the center of rotation of the eye may be performed directly in a reference frame based on the spectacle frame. Determining the position of the lens then simply involves centering the lens in the spectacle frame, using either the usual parameters for boxing, or, as explained below, with measurement under conditions of natural posture of directions of the wearer's gaze.

The implementation of the manufacture of the lens is also facilitated by the use of such a reference frame, especially if the step 10 of measuring the position of the center of rotation of the eye is not carried out at the same place as the calculation step; it is sufficient that the two places involved in the manufacture can make use of the same model of frame.

The reference frame can also be a reference frame that is linked to the eye. A reference frame linked to the eye is a reference frame one axis of which is the primary direction of gaze. This makes it possible to obtain a calculating step that is easier to implement because the ray tracing is performed in a reference frame one of the axes of which is the main optical axis of the eye-lens optical system.

One can equally as well use a reference frame calculated on the basis of the three-dimensional coordinates of each of the centers of rotation of the wearer. We can define such a reference frame notably as follows:

choose the first axis passing through the two centers of rotation measured choose the second axis to include the perpendicular bisector of the segment defined by the two centers of rotation and parallel to the Frankfurt plane choose the third axis to be perpendicular to the two previous axes.

This has the advantage of enabling the head to be positioned relative to the object space and to govern the kinematics of both eyes turning around their center of rotation.

Measurements step 10 can be carried out under conditions of natural posture of the wearer. By natural posture we mean the natural tendency of a wearer to take a preferred position of the head which is not that with the head held straight when he looks at a reference point. The preferred position can be characterized by angles of posture with respect to a reference posture that can be for example be the posture with the head held straight. Taking into account the conditions of the natural posture makes it possible to obtain a lens that is even better suited to the needs of the wearer. Compared to the traditional method, which assumes that the wearer always holds the head straight for far vision, measurement under conditions of natural posture makes it possible to better take account of the actual position of the wearer. For example, if the wearer has, in far vision, his or her head slightly bent forward, the area of far vision will be higher up on the lens when compared to the position of the area for far vision in a traditional lens. Similarly, it is also possible to take into account the condition of natural posture when the wearer is looking in conditions of near vision, such as when the wearer is reading a document. For example, if the wearer in conditions of near vision has his or her head slightly tilted to one side, the area in conditions of near vision will be shifted to the same side of the lens compared the position of the near vision area in a traditional lens. In the traditional method, it is assumed that the wearer always looks at an object in the sagittal plane when looking in conditions of near vision.

Figure 14:
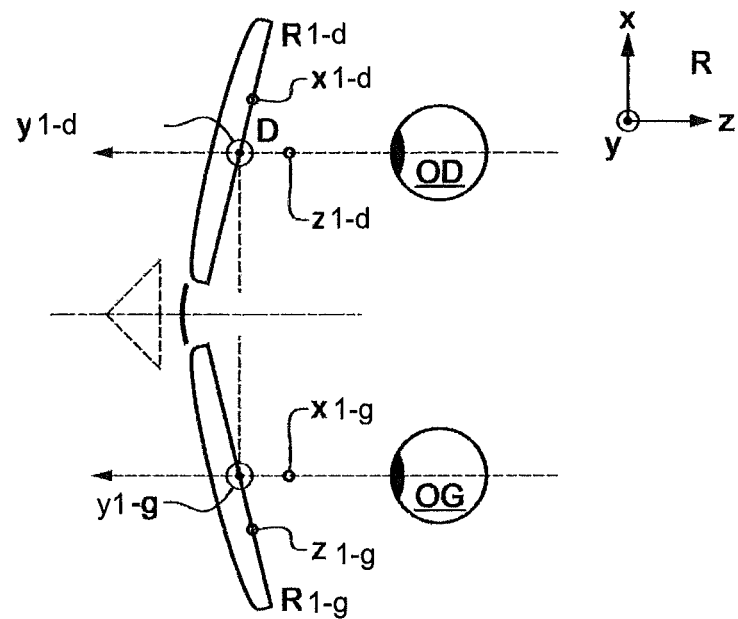
FIGS. 14 to 16 are diagrammatic illustrations of the effect of a non-zero head posture.

Another method as shown by the flowcharts of FIGS. 1 and 2 is to perform a further step 15 in which at least one direction of gaze in a natural posture is measured. The effect of a non-zero head posture on the ophthalmic correction for a wearer is particularly illustrated when we compare FIGS. 14 and 15. These two Figures correspond to a particular illustration for natural horizontal position when the wearer looks in far vision. A similar illustration would make it possible to highlight the effect of a natural vertical non-zero posture. In FIG. 14, two eyes with their corrective lens are shown. In this situation, the natural posture of the head is that with the head held straight, that is to say, a head posture of zero. The coordinates of the center of rotation of the left eye noted OG and for the right eye noted OD are given in a reference frame for calculation R which is chosen arbitrarily. The reference frame for calculation R is a three-dimensional reference frame the axes of which are the x, y and z axes. In this reference frame R, the coordinates xg, yg and zg are those of the center of rotation of the left eye and the coordinates xd, yd, and zd are those of the center of rotation of the right eye. Each lens is positioned and oriented with respect to the corresponding center of rotation. Each lens consequently has its own inclination which is bound to the frame. We can thus define for each lens, a specific three-dimensional reference frame noted $R_{1\_g}$ for the lens of the left eye and $R_{1\_d}$ for the lens of the right eye.

According to FIG. 14, the origin of the reference frame $R_{1\_g}$ is the point G which corresponds to the point of intersection of the primary direction of gaze (gaze direction of the wearer when asked to look straight ahead into the distance) and the back of the lens. Thus, if the axes of the reference frame $R_{1\_g}$ are noted $x_{1\_g}$, $y_{1\_g}$ and $z_{1\_g}$, the axis $y_{1\_g}$ is parallel to the y-axis while the axis $x_{1\_g}$ is tangent to the rear face of the lens at G. The axis $x_{1\_g}$ is such that $x_{1\_g}$, $y_{1\_g}$ and $z_{1\_g}$ form a right-handed trihedron. As a result, the axis $z_{1\_g}$ is normal to the rear surface at G. In addition, the reference frame for the left lens $R_{1\_g}$ is deduced from the reference frame R by rotation through an angle βg about the y-axis in the (x, z) plane, rotation being performed as per trigonometric convention, i.e. counterclockwise. Thus, an angle βg is made between firstly, the axes $x_{1\_g}$ and x and, secondly, the axes $z_{1\_g}$ and z. The angle βg is bound to the frame.

According to FIG. 14, the origin of reference frame $R_{1\_d}$ is the point D which corresponds to the intersection of the primary direction of gaze (gaze direction of the wearer when asked to look ahead into the distance) and the back of the lens. Thus, if the axes of the reference frame $R_{1\_d}$ are noted $x_{1\_d}$, $y_{1\_d}$ and $z_{1\_d}$, axis $y_{1\_d}$ is parallel to the y-axis while the axis $x_{1\_d}$ is tangent to the rear face of the lens at D. The axis $x_{1\_d}$ is such that $x_{1\_d}$, $y_{1\_d}$ and $z_{1\_d}$ form a right-handed trihedron. As a result, the axis $z_{1\_d}$ is normal to the rear surface at D. In addition, the reference frame for the left lens $R_{1\_d}$ is deduced from the reference frame R by rotation through an angle βd about the y-axis in the (x, z) plane, rotation being in the anti-trigonometric sense, i.e. clockwise. Thus, an angle -βd is made between firstly, the axes $x_{1\_d}$ and x and, secondly, the axes $z_{1\_d}$ and z. The angle βd is linked to the frame.

Figure 15:
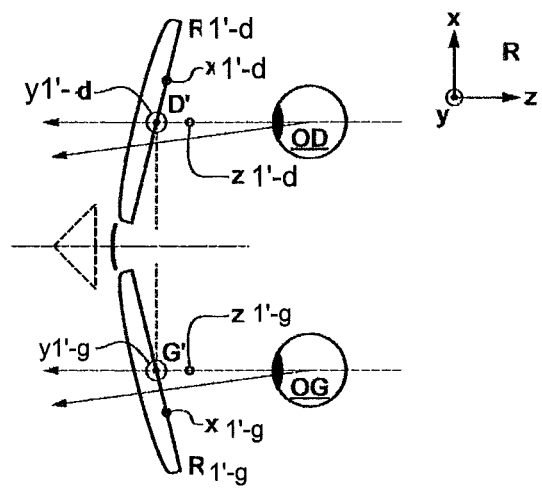

Similarly to the case of FIG. 14, we define specific three-dimensional reference frames noted $R_{1'\_d}$ for the lens of the left eye and $R_{1'\_d}$ for the lens of the right eye in the case of FIG. 15. In the situation of FIG. 15, the natural posture of the head is non-zero. For the sake of simplicity, all previous definitions and notations, primed (') are re-employed for reference frames linked to the spectacle frame. Thus, the x-axis and $x_{1'\_g}$ on the one hand and $z_{1'\_g}$ and z on the other make an angle of β'g with each other. Similarly, the axes x and $x_{1'\_d}$ on the one hand and $z_{1'\_d}$ and z on the other make an angle of -β'd with each other. The intersection of the primary direction of gaze with the rear face of the lens in the left eye is noted G' and the intersection of the primary direction of gaze with the rear face of the lens of the right eye is noted D'. To aid understanding, there is illustrated in FIG. 15 both the primary direction of gaze in the case of a natural posture of the head that is non-zero (illustrated by solid arrows) and the primary direction of gaze in the case of a natural posture of the head which is zero (shown by the arrows in dotted lines).

Figure 16:
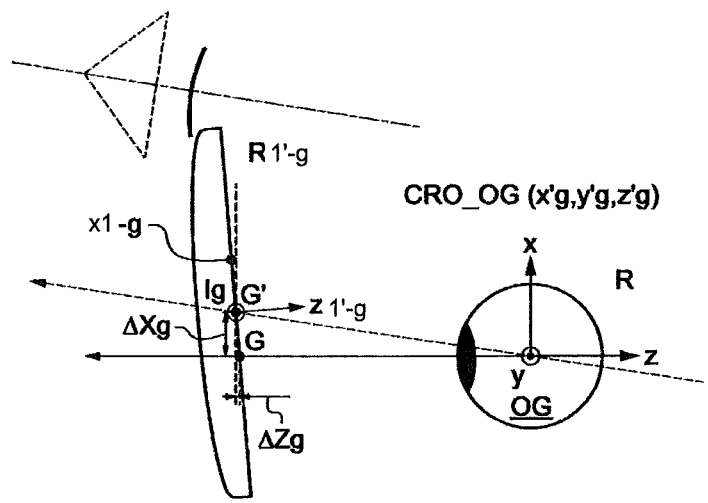
Figure 17:
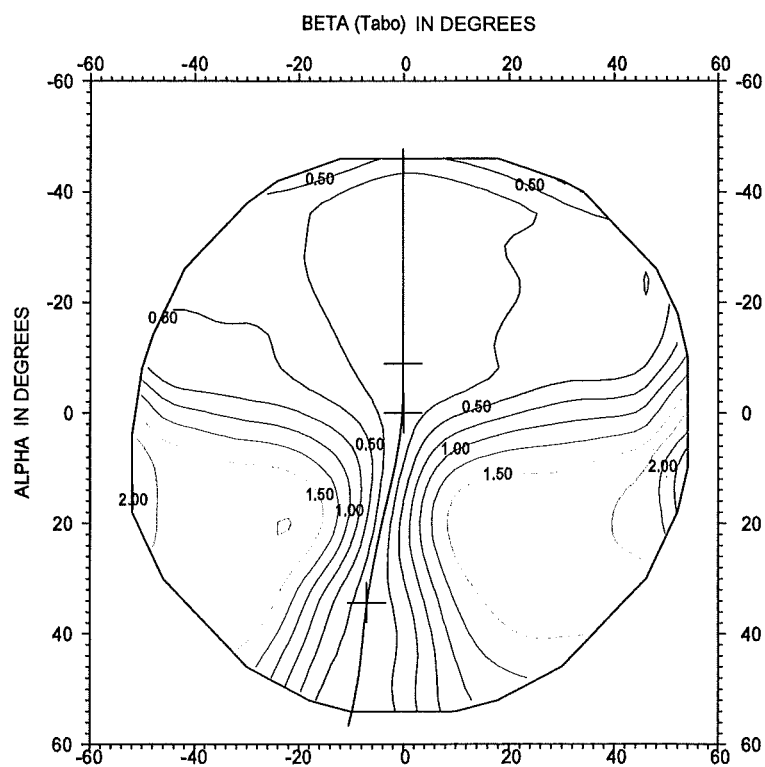
FIGS. 17 to 21 show graphically astigmatism defects for several lenses according to whether parameters of posture are taken into account or not.

FIG. 16 is an enlarged view of FIG. 15 for the left eye. Compared to FIG. 15, it is noted that the inclination of the lens in the plane formed by axes x and z is a natural posture gets changed between a zero natural horizontal posture and a non-zero natural horizontal posture. This means that the angles βg and β'g are not the same. The other change concerns the respective positions of G and G'. To facilitate comparison, point G has been marked in FIG. 16, bearing in mind that it no longer corresponds to the primary direction of the wearer in a natural posture. This nevertheless allows us to observe that the lens is offset by an amount ΔXg along the x axis and distanced by an amount ΔZg along the z axis from the center of rotation of the left eye OG. The amount ΔXg is the difference in coordinates along the x axis between the point G' and the point G while the amount ΔZg is the difference in coordinates along the z axis between the point G' and the point G. Similarly, although the enlarged figure is not shown, the angles βd and β'd are different and the lens of the right eye is offset by an amount ΔXd along the x axis and distanced by an amount ΔZd along the z axis from the center of rotation of the right eye OD. The amount ΔXd is the difference in coordinates along the x axis between the point D' and point D while the amount ΔZg is the difference in coordinates along the z axis between the point D' and the point D.

Thus, the comparison between FIGS. 14 to 16 shows that the positions and orientations of the lenses in the case of a non-zero head posture are different from the situation with zero head posture. This implies that head posture leads to changes in lens use.

These changes are also reflected when we compare the performance of lenses under conditions of use shown illustrated starting from FIGS. 17 to 21 which are maps showing the astigmatism defect for lenses with the same prescription as the lenses of FIGS. 6-13 discussed above. One such performance is represented by the astigmatism defect maps of FIGS. 17 and 18. These defects of astigmatism are represented in a reference frame associated with the left eye as defined in FIG. 24. For both maps, directions of gaze are expressed in the original reference frame defined when the wearer had zero head posture. The direction of gaze (α=0; β=0) is the primary direction of gaze when the head posture is zero. The map of FIG. 17 corresponds to the case of zero head posture while in the case of the map according to FIG. 18, the wearer has a non-zero head posture with the result that β'g=βg-5°. This shows that a non-zero head posture changes the distribution and amount of astigmatism over the lens when it the latter was optimized for the condition of zero head posture. For example, in FIG. 17, the astigmatism defect in the direction of far vision is 0.00 diopters and in the direction of near vision is 0.13 diopters, and in FIG. 18, the astigmatism defect in the direction far vision is 0.05 diopters and in the direction of near vision is 0.49 diopters. In addition, a loss of left/right symmetry is observed at either side of the meridian 12 in FIGS. 17 and 18. The meridian corresponds to the mean direction of gaze when the wearer glances from far vision to near vision. In addition, the isoastigmatism curves are shifted to the nasal side.

The effects demonstrated previously for a non-zero horizontal head posture also exist in the case of a vertical head posture which is not zero. In such a situation, the vertical angle of inclination about the x axis in the y, z plane would become modified and the lens would be off-centered vertically along the y axis and brought closer to or, respectively, moved away from the center of optical rotation depending on which eye is considered. In addition, in the case of a non-zero horizontal head posture and a non-zero vertical head posture, there would be a combination of the aforementioned effects, namely a change in the horizontal and vertical angles of inclination along with both horizontal and vertical off-centering of the lens and a change of the distance between the lens and the center of rotation of the relevant eye. By the mean distance between the lens and the center of rotation of the eye, we mean the distance between the intersection of the primary direction of gaze with the rear face of the lens on line z and the center of rotation of the eye.

As a result, the position of the lens with respect to the center of rotation of the eye and notably the directions of gaze adopted for the calculations of power and astigmatism are more representative of reality when we take natural posture into consideration, rather than an average position determined by statistical methods or zero head posture.

Figure 18:
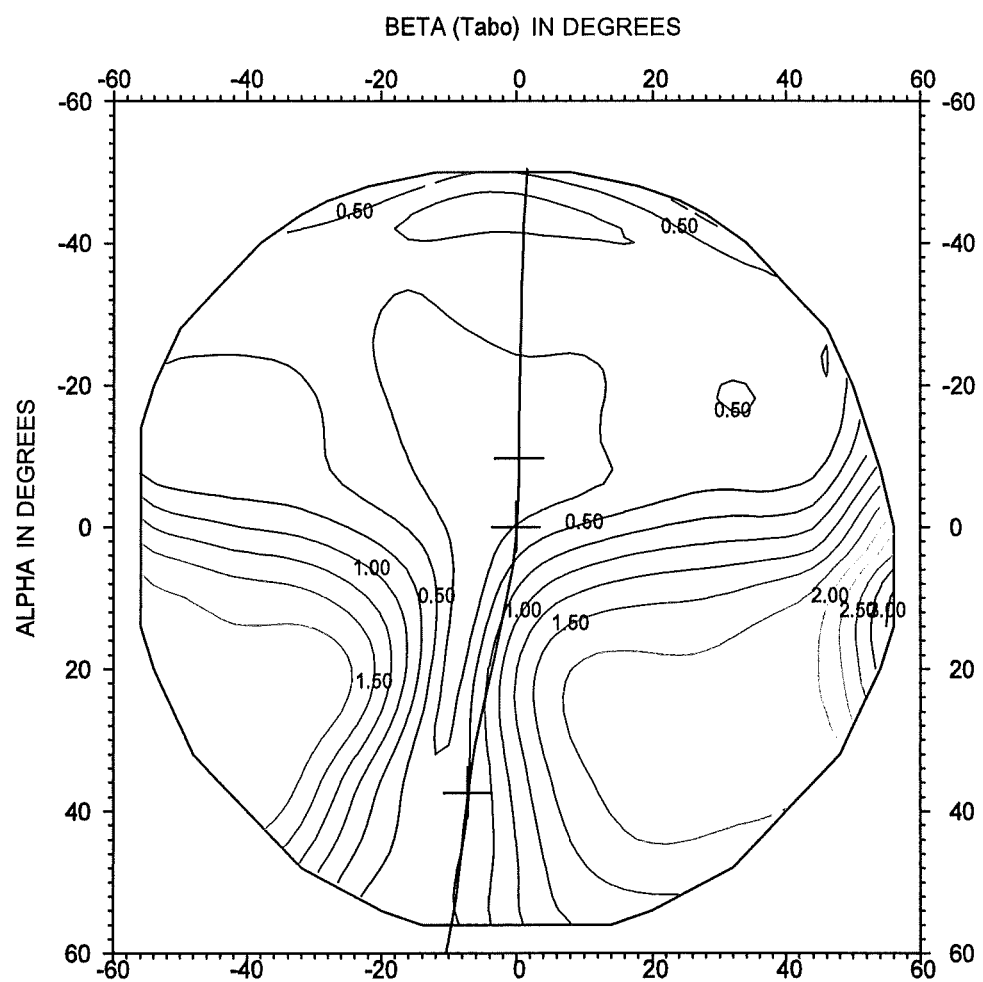
Figure 19:
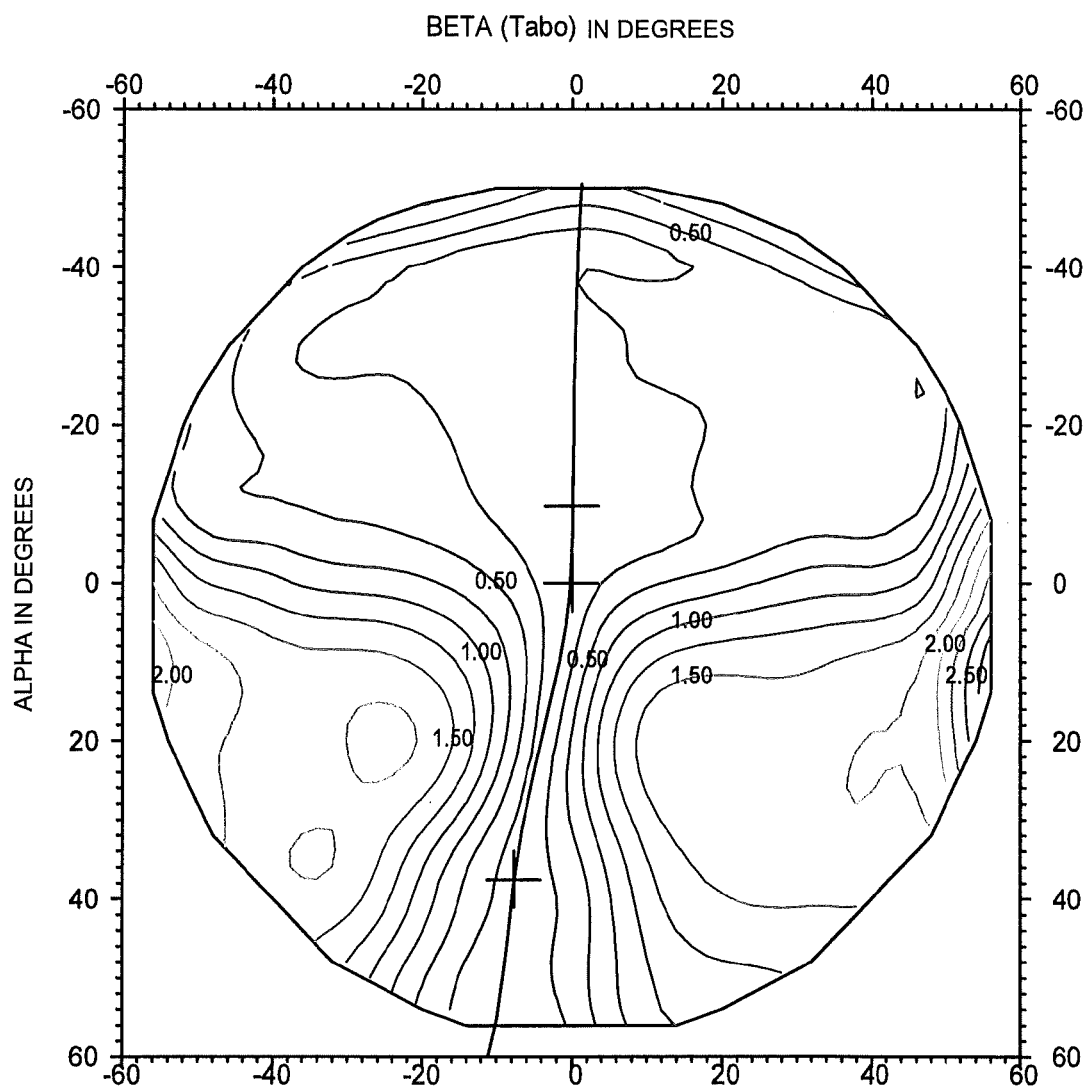

Such a benefit can be demonstrated when we compare FIGS. 18 and 19. These each show maps representing the astigmatism defect for two lenses. For each of the these figures, the natural horizontal posture of the wearer is such that $\beta'g=\beta g-5°$. These defects of astigmatism are represented in a reference frame associated with the left eye as defined in FIG. 24. For both maps, directions of gaze are expressed in the original reference frame set when the wearer had zero head posture. The direction of gaze ($\alpha=0$; $\beta=0$) corresponds to the primary direction of gaze when head posture is zero. For the lens according to the example in FIG. 18, the position was not taken into account when calculating the characteristics of the ophthalmic lens while in the case of the lens according to the example in FIG. 19, the natural posture of the wearer was included in the calculation of the characteristics. It is thus possible to see that the distribution of astigmatism is different between the two situations. In particular, in FIG. 18, the astigmatism defect in the direction of far vision is 0.05 diopters and in the direction of near vision is 0.49 diopters, and in FIG. 19, the astigmatism defect in the direction of far vision is 0.00 diopters and in the direction of near vision is 0.18 diopters. In addition, the symmetry of the distribution of astigmatism defect is found again when compared to the situation where head posture is zero (see FIG. 17). Taking into account the natural posture of the wearer in the calculation of the ophthalmic lens therefore allows a better adaptation of the lens to the wearer.

Figure 20:
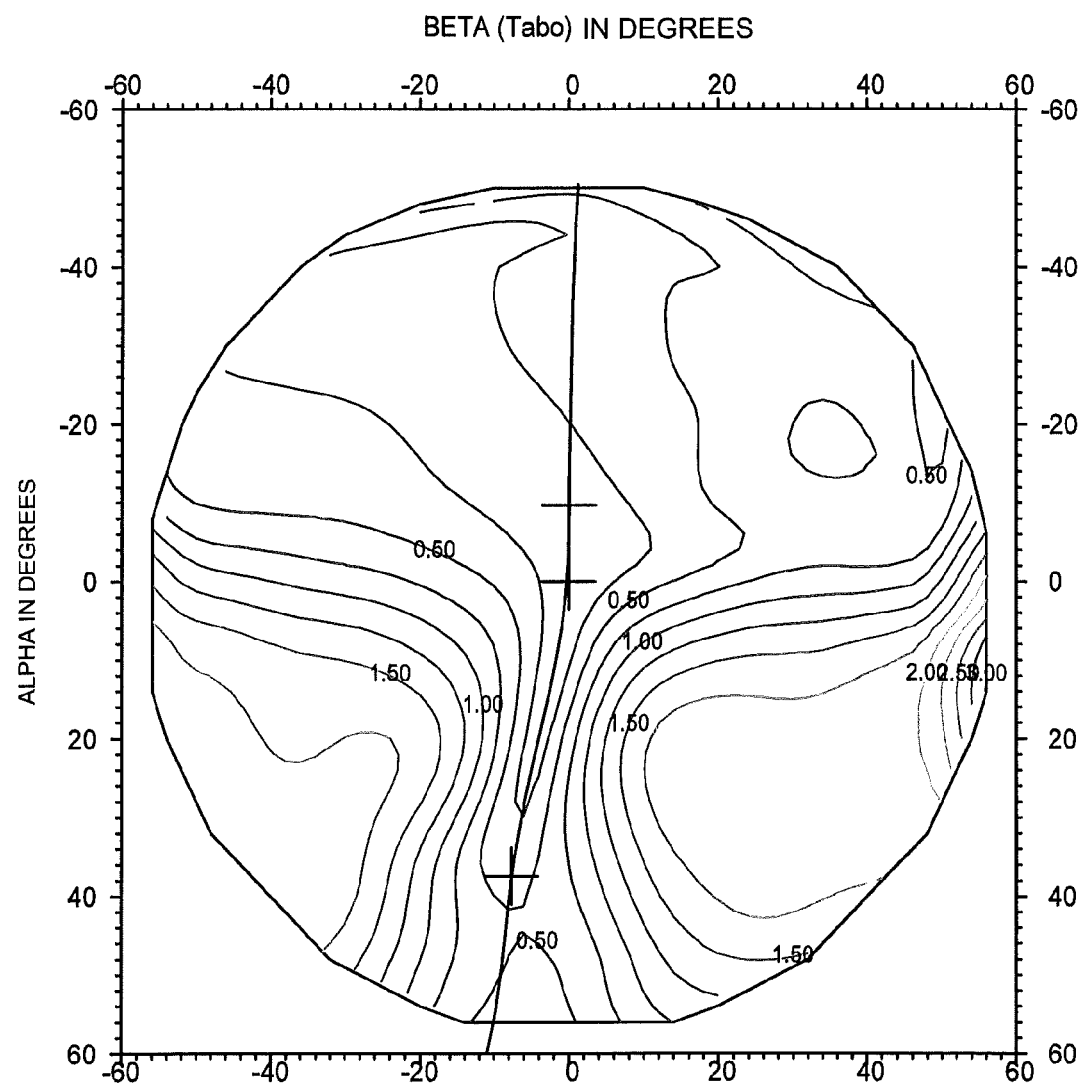
Figure 21:
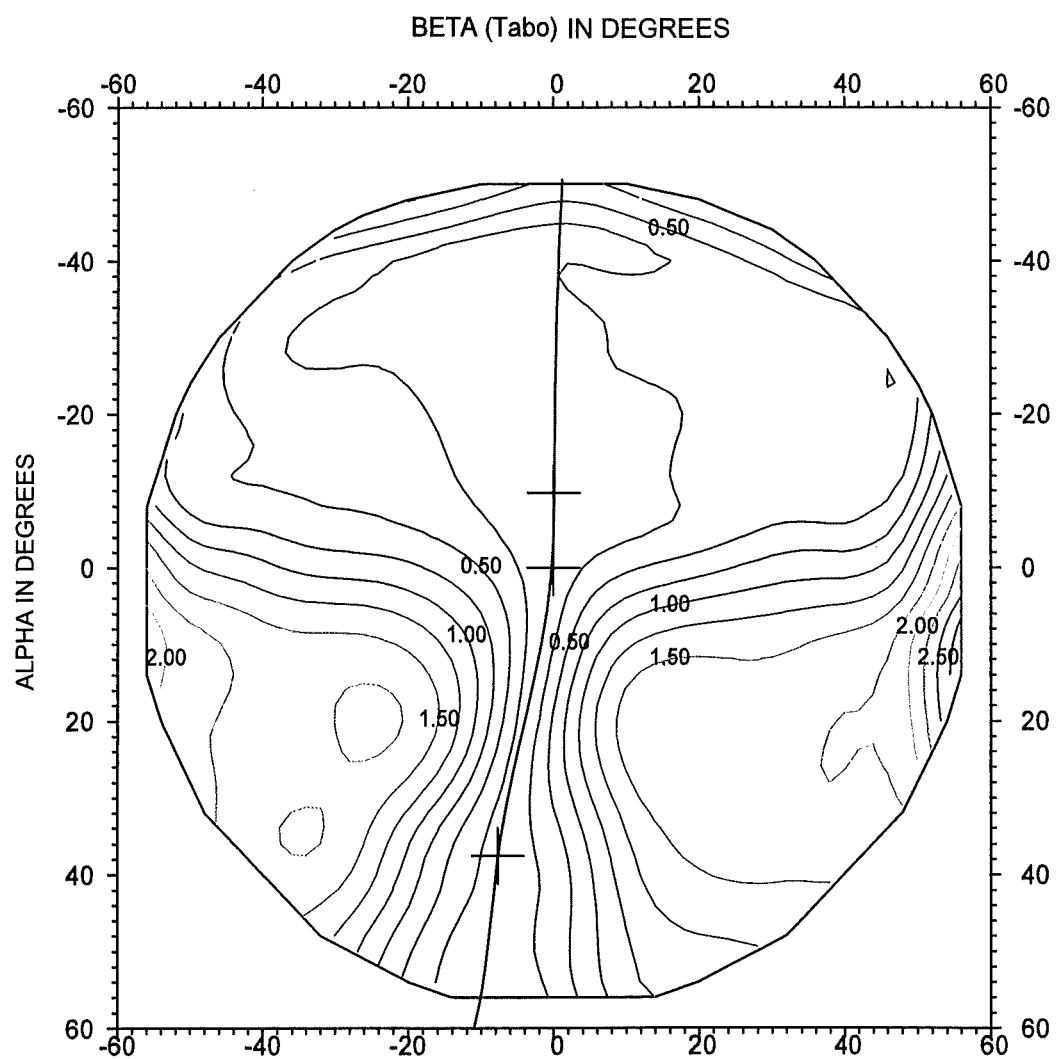

According to one embodiment, it is possible to not to take account of the effects of off-centering brought about by the natural posture of the wearer in the calculation. Only the change in orientation of the lens and the change in the distance between the lens and the center of rotation of the relevant eye are then taken into account in determining the characteristics of the lens. This simplifies the calculation while maintaining good performance for the lens because the optician can, during the operation of centering, compensate for the effect of off-centering by off-centering the lens. This is what is shown in the examples of FIGS. 20 and 21. These are each maps representing astigmatism defect for two lenses. For each of these Figures the natural horizontal posture of the wearer is such that $\beta'g=\beta g-5°$. These defects in astigmatism are represented in a reference frame associated with the left eye as defined in FIG. 24. For both maps, directions of glance are expressed in the original reference frame set when the wearer has zero head posture. The direction of gaze ($\alpha=0$; $\beta=0$) is the primary direction of gaze when the head posture is zero. The lens according to the example in FIG. 20 was obtained by not taking into account any effect due to the non-zero head posture (changing the orientation of the lens, changing the distance between the lens and the center of rotation of the eye, induced off-centering) in the calculation. In contradistinction, when calculating the lens according to the example in FIG. 21, a change in the orientation of the lens and a change in the distance between the lens and the center of rotation of the eye were taken account of. In both cases, the effect of off-centering was taking account of by the optician when perfoE using the centering operation. It is observed that when no effect is taken into account during calculation but the effect of off-centering is compensated for by the optician, the isoastigmatism lines do not get shifted to the nasal side. When compared to FIG. 18, this can be explained by the operation performed by the optician. However, the distribution of astigmatism defects is different from the case of FIG. 17 corresponding to a zero natural posture and the symmetry of distribution is lost. This is not the case for the lens in the example in FIG. 21. This shows clearly that simply taking account of a change in the orientation of the lens and a change in the distance between the lens and the center of rotation of the relevant eye in the calculation makes it possible to once more find the performance of the optimized lens with a condition of zero head posture provided that the optician compensates for the off-centering brought about by the non-zero head posture.

The use of measurement of the center of rotation of the eye in binocular vision is also proposed in a method for calculating the parameters for trimming an ophthalmic lens for a wearer and a frame chosen by the wearer.

Figure 3:
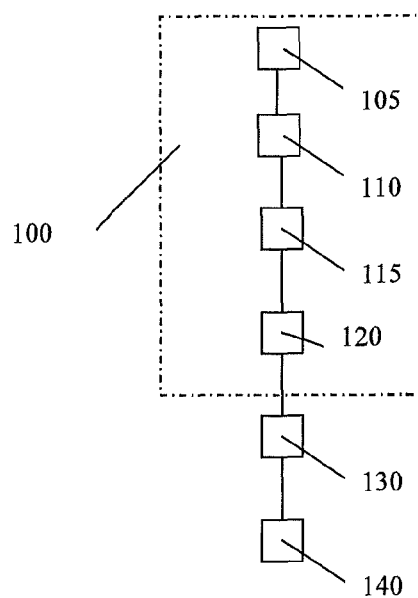
FIG. 3 is a flowchart of an example of the implementation of a method for calculating the parameters for trimming of an ophthalmic lens.

FIG. 3 is a flowchart for the implementation of such a method. The method includes a step 100 of determining an ophthalmic lens according to the method of determination discussed above with reference to FIGS. 1 and 2. Thus, according to the example in FIG. 3, step 100 includes three steps consisting in step 105 for measuring the position of the center of rotation of the eye in binocular vision in a reference frame, step 110 for measuring the position of the pupil in the reference frame, step 115 for measuring at least one direction of gaze in a natural posture and step 120 for determining the position of the spectacle frame with respect to the center of rotation of the eye.

Step 130 is a step for calculating the characteristics of the lens, from a starting lens positioned at the desired position relative to the center of rotation of the eye.

The method also includes a step 140 for calculating the trimming parameters of the ophthalmic lens according to the position of the lens and the spectacle frame in the reference frame. Knowledge of the trimming parameters allows the contour of the lens to be machined or cut to fit the frame chosen by the wearer. Once used, the trimming information obtained allows lenses particularly well suited to the wearer to be obtained.

This is especially true when using a measurement of the direction of gaze of the wearer in a natural posture. Instead of considering the directions of gaze far an average wearer—for instance a direction of gaze in far vision with the head held straight—we can take account of the natural posture of the wearer, either horizontally or vertically.

The use of lens trimming information or data is done when the lens is trimmed, which can be performed in the same place as the place where step 130 of calculation was carried out or in a different place.

More generally, other data sets can be used for the manufacture of a lens. For example, a data set may include three-dimensional coordinates, measured on a wearer in binocular vision, the center of rotation of one eye of a wearer, expressed in a reference frame. The data set also includes position in the same reference frame of a spectacle frame. The data set may also include angles representing natural posture of the wearer in the same reference frame. Such data sets have the advantage of allowing lenses well suited to the wearer to be obtained by calculation.

Figure 4:
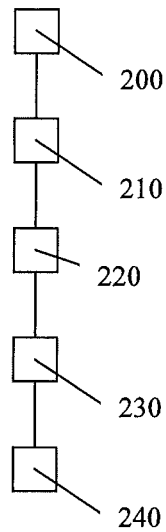
FIG. 4 is a flowchart of an example of the implementation of a method for producing an ophthalmic lens.

Thus, the data sets discussed above can be used in a particular method of manufacturing a lens. FIG. 4 is a flowchart of an example of implementation of such a method. The method includes a step 200 of measuring on the wearer in binocular vision, three-dimensional coordinates of the center of rotation of a wearer's eye in a reference frame at a first location. The first location can in particular be a point of sale of the lenses. At this measurement step 200 measurement of the position of a frame chosen by the wearer is also performed in the same reference frame.

The manufacturing method also includes a step 220 for transmitting the measured coordinates and position to a second location. The second location may be particularly a prescription laboratory producing lenses having the characteristics of the wearer's prescription from semi-finished lenses. At transmission step 220, it is possible to transmit other data such as the wearer's prescription that the ophthalmologist or optician usually notes as a triplet (sphere, cylinder, and axis) in a particular convention i.e. "positive cylinder" or "negative cylinder". As the ophthalmologist (or the optician) can also measure the frame wearing conditions specific to the wearer, lens-eye distance, pantoscopic angle and the curve of the selected frame can notably also be transmitted at transmission step 220.

The manufacturing method also includes a step 230 for determining, at the second location, the lens by calculating the characteristics of the lens by tracing rays through the measured center of rotation of the eye starting out from an initial lens positioned in the reference frame with respect to the center of rotation of the eye.

The manufacturing method also includes a step 240 of manufacturing the lens that's determined. Manufacturing can be implemented at any location. This can be the first and second location, but another location is possible. For example, the prescription laboratory can receive the data transmitted at transmission step 220 at a second location and implement manufacturing in a third location. The second location may be a processing center for the data transmitted and the third location a lens factory. Such a method has the advantage of allowing lenses to be made more quickly, the lens being able to be made immediately after measurement.

The manufacturing method may also include the steps of measuring the position of the spectacle frame in the reference frame used for the determination, of calculating the trimming parameters of the ophthalmic lens as a function of the position of the lens and of the spectacle frame in the reference frame and trimming of the lens. This provides a trimmed lens tailored to the wearer.

The method may further include a step 210 consisting in measuring, at as first location, angles representative of the natural posture of the wearer in the reference frame. According to the example in FIG. 4, step 210 of measuring the natural posture takes place after measuring, for the wearer in binocular vision, three-dimensional coordinates of the center of rotation of the wearer's eye. However, it is possible to perform both measurement steps 200, 210 in a different order.

The transmission step 220 can then include transmission of the angles of posture measured and a determination step 230 can make use of the measured angles of postures. The lens produced is thus better adapted to the wearer.

Figure 5:
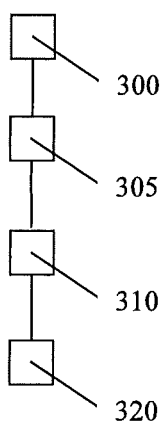
FIG. 5 is a flowchart of an example of the implementation of a method for simulation of an ophthalmic lens.

The use of measurement from the center of rotation of the eye in binocular vision is also proposed for a simulator of the image seen by a wearer through an ophthalmic lens. Such a simulator is thus suitable for implementing a method of simulating an image seen by a wearer through an ophthalmic lens. FIG. 5 illustrates a flowchart of an example of the implementation of such a method of simulation. The simulation method includes a step of measurement 300, on the wearer in binocular vision, of the three-dimensional coordinates of the center of rotation of a wearer's eye in a reference frame. As an illustration, like the determination method discussed above, the reference frame may be a reference frame associated with the wearer's head, a reference frame optionally associated with the spectacle frame when a spectacle frame has been chosen, or a reference frame linked to the eye.

The simulation method also includes a step 305 for measuring at least one direction of gaze in a natural posture.

The simulation method also includes a step 310 for positioning the lens in the same reference frame.

The method also includes a step 320 for calculating an image seen by the wearer using tracing of rays through the center of rotation of the eye and the lens. As the method of simulation takes account of the actual position of the center of rotation of the eye, the simulated image is closer to reality that if a position approximated to the center of rotation of the eye had been taken into account. The calculation also takes account of the direction of gaze measured in a natural posture.

The simulation method can further include a measuring step in the reference frame for the position of the pupil of the eye. The calculation step 320 then employs the measured position of the pupil. This helps to better simulate the image because the impact on the image of out-of-field aberrations that depend on the size of the pupil is calculated more accurately.

The simulator allowing the implementation of this method includes calculation means adapted to implement the simulation method; known data entry means can be associated therewith. The simulator also includes means for displaying the calculated image. This means that the wearer can be shown the difference between a lens according to the invention and a conventional lens, to allow him or her to appreciate the effects of the invention.

In the description above, we have seen that the method for determining an ophthalmic lens for an eye of a wearer comprises a calculation step the characteristics of the ophthalmic lens using the measured coordinates and the determined position. We have also seen that this calculation step can take the form of either a step modifying the starting ophthalmic lens by wavefront analysis or, alternatively, by optimization, from the starting lens, by tracing rays dependent on the coordinates measured and the determined position. Other alternative embodiments are also possible. For example, as a third alternative, in the calculation step, the characteristics of the ophthalmic lens are calculated by local modification of the ophthalmic lens at the point of impact with the mean ray passing through the center of rotation of the eye measured for a given direction of gaze. According to this third alternative, it is possible to obtain desired optical characteristics from, for example, pre-calculated data, stored in a database. This pre-calculated data may for example consist of surface pieces or geometric characteristics to be applied locally to the surface, for example, a radius of curvature or aspheric coefficients.

The invention claimed is:

1. A method for determining an ophthalmic lens for an eye of a wearer, the method comprising the steps of:
    measuring, on the wearer in binocular vision, three-dimensional coordinates of a center of rotation of the wearer's eye;
    measuring at least one direction of gaze in a natural posture;
    determining a desired position of the ophthalmic lens; and
    calculating characteristics of the ophthalmic lens by using the coordinates measured for the center of rotation of the eye, the determined position of the lens and the at least one direction of gaze measured in a natural posture, the characteristics of the ophthalmic lens calculated by positioning a starting ophthalmic lens in the determined position and at least one of modifying the starting ophthalmic lens by wavefront analysis or starting from the starting ophthalmic lens, optimizing using ray tracing dependent on the coordinates measured for the center of rotation of the eye and the determined position of the lens.

2. The method according to claim 1, wherein the method comprises a step of measuring on the wearer in binocular vision, the position of a pupil of the eye with respect to the center of rotation of the eye and in which the calculation step employs the measured position of the pupil.

3. The method according to claim 1, wherein the calculation step is performed in a reference frame based on at least one of the wearer's head, a spectacle frame, or the wearer's eye.

4. The method according to claim 1, further comprising a step of measuring on the wearer in binocular vision, three-dimensional coordinates of the center of rotation of each eye of the wearer and in which the calculation step is done in a reference frame that is based on three-dimensional coordinates of the center of rotation of each eye of the wearer.

5. The method according to claim 1, wherein the step of measuring three-dimensional coordinates of the center of rotation of the eye is performed under conditions of natural posture of the wearer.

6. The method according to claim 1, wherein the center of rotation of the eye is the center of optical rotation.

7. The method according claim 1, wherein the at least one direction of gaze measured in a natural posture is the primary direction of gaze.

8. The method according to claim 7, wherein, in the step of measuring the at least one direction of gaze, a distance of the lens to the center of rotation of the eye is measured corresponding to the distance between the intersection of the primary direction of gaze with a rear face of the lens and the center of rotation of the eye, and at the calculation step, the calculation employs said measured distance.

9. The method according claim 1, wherein the at least one direction of gaze measured in a natural posture is the direction of gaze when the wearer is looking in conditions of near vision.

10. The method according to claim 1, in which several directions of gaze are measured in a natural posture.

11. The method according claim 1, wherein at the step of measuring the at least one direction of gaze, an orientation of the lens and a lens position are measured, and at the calculation step, calculation employs said measured orientation of the lens and position of the lens.

12. The method for determining an ophthalmic lens according to claim 1, characterized in that during the calculation step the characteristics of the ophthalmic lens are calculated by local modification of the ophthalmic lens at the point of impact with an average ray passing through a center of rotation of the eye measured for a given direction of gaze.

13. A method for calculating parameters for preparing an ophthalmic lens for a wearer and a spectacle frame chosen by the wearer, comprising the steps of:
    determining an ophthalmic lens according to a method comprising the steps of:
    measuring, on the wearer in binocular vision, three-dimensional coordinates of a center of rotation of the wearer's eye using a reference frame; measuring at least one direction of gaze in a natural posture; determining a desired position of the ophthalmic lens using the reference frame; and calculating characteristics of the ophthalmic lens by using the coordinates measured for the center of rotation of the eye, the determined position of the lens and the at least one direction of gaze measured in a natural posture, the characteristics of the ophthalmic lens calculated by positioning a starting ophthalmic lens in the determined position and at least one of modifying the starting ophthalmic lens by wavefront analysis or starting from the starting ophthalmic lens, optimizing using ray tracing dependent on the coordinates measured for the center of rotation of the eye and the determined position of the lens;
    measuring a position of the spectacle frame in the reference frame; and
    calculating parameters for preparing the ophthalmic lens according to the position of the lens and the spectacle frame in the reference frame, the preparing of the ophthalmic lens including at least one of mounting or trimming of the ophthalmic lens.

14. A method of simulating an image seen by a wearer through an ophthalmic lens, comprising the steps of:
    measuring, on the wearer in binocular vision, three-dimensional coordinates of the center of rotation of the wearer's eye;
    measuring at least one direction of gaze in a natural posture;
    positioning of the lens, the steps of measuring and positioning taking place in or being reduced to the same reference frame;
    measuring, in the reference frame, the position of the pupil of the eye; and
    calculating an image seen by the wearer using ray tracing, taking into account the measured position of the center of rotation of the eye, the direction of gaze measured in a natural posture and position of the lens, the calculation step employing the measured position of the pupil.

15. A method for producing an ophthalmic lens, comprising the steps of:
    measuring on a wearer in binocular vision, three-dimensional coordinates of the center of rotation of the wearer's eye and a position of a spectacle frame chosen by the wearer, in the same reference frame, at a first location;

measuring at least one direction of gaze in a natural posture, transmitting the measured coordinates and position to a second location;

determining the lens by calculation using the measured coordinates and position, at the second location, the calculation including positioning a starting ophthalmic lens in the position and at least one of modifying the starting ophthalmic lens by wavefront analysis or starting from the starting ophthalmic lens, optimizing using ray tracing dependent on the measured coordinates and the position; and manufacturing the lens so determined.

16. The method according to claim 15, further comprising a step of measuring angles representing a natural posture of the wearer in the reference frame at the first location, in which the transmission step includes the transmission of measured 5 angles and posture the determination step employs the measured angles of posture.

17. The method according to claim 15, further comprising a step of:

measuring the position of the spectacle frame in the reference frame used for the determination;

calculating trimming parameters for the ophthalmic lens as a function of the position of the lens and the spectacle frame in the reference frame, and trimming of the lens.

18. A simulator of an image seen by a wearer through an ophthalmic lens, the simulator configured to perform the steps of:

receiving three-dimensional coordinates of the center of rotation of the wearer's eye measured on the wearer in binocular vision using a reference frame;

receiving at least one direction of gaze measured in a natural posture;

receiving a position of the lens in the reference frame, calculating an image seen by the wearer using ray tracing, taking into account the measured position of the center of rotation of the eye, the direction of gaze measured in a natural posture and position of the lens, the calculation including positioning a starting ophthalmic lens in the position and at least one of modifying the starting ophthalmic lens by wavefront analysis or starting from the starting ophthalmic lens, optimizing using ray tracing dependent on the measured coordinates and the position; and displaying the image.

19. One or more non-transitory computer-readable storage media storing computer-executable instructions for performing a method on a computing system, the method comprising the steps of:

receiving three-dimensional coordinates of the a center of rotation of the wearer's eye measured on the wearer in binocular vision;

receiving at least one direction of gaze measured in a natural posture;

receiving a determined position of the ophthalmic lens; and calculating characteristics of the ophthalmic lens by using the coordinates measured for the center of rotation of the eye, the determined position of the lens and the at least one direction of gaze measured in a natural posture, the characteristics of the ophthalmic lens calculated by positioning a starting ophthalmic lens in the determined position and at least one of modifying the starting ophthalmic lens by wavefront analysis or starting from the starting ophthalmic lens, optimizing using ray tracing dependent on the coordinates measured for the center of rotation of the eye and the determined position of the lens.

20. One or more non-transitory computer-readable storage media storing computer-executable instructions for performing a method on a computing system of simulating an image seen by a wearer through an ophthalmic lens, the method comprising the steps of:

measuring, on the wearer in binocular vision, three-dimensional coordinates of the center of rotation of the wearer's eye;

measuring at least one direction of gaze in a natural posture, positioning of the lens in a determined position, the steps of measuring and positioning taking place in or being reduced to the same reference frame, calculating an image seen by the wearer using ray tracing, taking into account the measured position of the center of rotation of the eye, the direction of gaze measured in a natural posture and position of the lens, the calculation including positioning a starting ophthalmic lens in the determined position and at least one of modifying the starting ophthalmic lens by wavefront analysis or starting from the starting ophthalmic lens, optimizing using ray tracing dependent on the measured coordinates and the determined position.

* * * * *